United States Patent
Dehghani et al.

(10) Patent No.: US 8,507,708 B2
(45) Date of Patent: Aug. 13, 2013

(54) ORGANOMETALLIC CATALYST AND PREPARATION THEREOF

(75) Inventors: Fariba Dehghani, Roseberry (AU); Zhong Xia, Chippendale (AU)

(73) Assignee: The University of Sydney, New South Wales (AU)

( * ) Notice: Subject to any disclaimer, the term of this patent is extended or adjusted under 35 U.S.C. 154(b) by 183 days.

(21) Appl. No.: 13/140,695

(22) PCT Filed: Dec. 18, 2009

(86) PCT No.: PCT/AU2009/001652
§ 371 (c)(1),
(2), (4) Date: Aug. 10, 2011

(87) PCT Pub. No.: WO2010/069000
PCT Pub. Date: Jun. 24, 2010

(65) Prior Publication Data
US 2011/0319645 A1     Dec. 29, 2011

(30) Foreign Application Priority Data
Dec. 19, 2008 (AU) ................................ 2008906549

(51) Int. Cl.
| | |
|---|---|
| C07F 13/00 | (2006.01) |
| C07F 11/00 | (2006.01) |
| C07F 15/00 | (2006.01) |
| C07F 5/06 | (2006.01) |
| C09K 3/00 | (2006.01) |

(52) U.S. Cl.
USPC ............ 556/131; 556/49; 556/61; 556/147; 556/183; 252/182.12

(58) Field of Classification Search
USPC ......... 556/49, 61, 131, 147, 183; 252/182.12
See application file for complete search history.

(56) References Cited

U.S. PATENT DOCUMENTS
2011/0319645 A1    12/2011   Dehghani et al.

FOREIGN PATENT DOCUMENTS
| EP | 0864361 | 9/1998 |
|---|---|---|
| WO | WO 2010/069000 | 6/2010 |

OTHER PUBLICATIONS

Rokicki and Kuran, "The Application of Carbon Dioxide as a Direct Material for Polymer Synthesis in Polymerization and Polycondensation Reactions", J. Macromol. Sci.-Rev. Macromo. Chem., 1981, C21(1), 135-136.

Soga, et al., "Alternating Copolymerization of CO2 and Propylene Oxide with Catalysts Prepared from Zn(OH)2 and Various Dicarboxylic Acids", Polymer Journal, 1981, 13, 407-410.

Soga, K., "Preparation of catalysts for the alternating copolymerization of propylene oxide and carbon dioxide" Nippon Kagakkaishi, 1982, 2, 295-300 (English Abstract).

(Continued)

*Primary Examiner* — Porfirio Nazario Gonzalez
(74) *Attorney, Agent, or Firm* — Woodcock Washburn LLP

(57) ABSTRACT

The present invention relates to a method for producing an organometallic catalyst and an organometallic catalyst when produced by the method. The method comprises the steps of combining a polycarboxylic acid or anhydride and a metal-oxide, metal-hydroxide or metal-salt with a solvent at a temperature and pressure at which the solvent exists as a supercritical or near-critical fluid. The polycarboxylic acid or anhydride is reacted with the metal-oxide, metal-hydroxide or metal-salt for sufficient time and under sufficient temperature and pressure to produce the organometallic catalyst. The present invention also relates to a process for making a poly (alkylene carbonate) in the presence of a catalytic amount of the organometallic catalyst produced by the method.

15 Claims, 12 Drawing Sheets

(56) References Cited

OTHER PUBLICATIONS

Wang, et al., "Synthesis and Characterization of Alternating Copolymer from Carbon Dioxide and Propylene Oxide", Journal of Applied Polymer Science, Jun. 2002, 85, 2327-2334.

Meng, et al., "Effects of the Structure and Morphology of Zinc Glutarate on the Fixation of Carbon Dioxide into Polymer", J. Polym. Sci.: Part A: Poly. Chem., Sep. 2002, 40, 3579-3591.

Hutchings, et al., "Amorphous Vanadium Phosphate Catalysts Prepared using Precipitation with Supercritical CO2 as an Antisolvent", Journal of Catalysis, May 2002, 208, 197-210.

International Patent Application No. PCT/AU2009/001652: International Preliminary Report on Patentability dated Mar. 21, 2011, 7 pages.

International Patent Application No. PCT/AU2009/001652: International Search Report dated Feb. 17, 2010, 2 pages.

ORGANOMETALLIC CATALYST AND PREPARATION THEREOF

CROSS-REFERENCE TO RELATED APPLICATIONS

This application is the National Stage of International Application No. PCT/AU2009/001652, filed Dec. 18, 2009, which claims the benefit of Australian Application No. 2008906549, filed Dec. 19, 2008, the disclosures of which are incorporated herein by reference in their entireties.

FIELD OF THE INVENTION

The present invention relates to catalysts and the synthesis thereof, and in particular to organometallic catalysts for polymerization reactions.

The invention has been developed primarily for use as a catalyst for copolymerizing carbon dioxide and epoxides to form poly(alkylene carbonates) and will be described hereinafter with reference to this application. However, it will be appreciated that the invention is not limited to this particular field of use.

BACKGROUND OF THE INVENTION

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

It is known in the prior art that high molecular weight polymers can be prepared by copolymerizing carbon dioxide with epoxy compounds in order to provide the corresponding poly(alkylene carbonates). The polymers which are produced are typically alternating copolymers of the carbon dioxide and epoxide monomers. Because such high molecular weight polymers decompose relatively cleanly, they find use in foam moulding applications and as binders for ceramic or metallic particles in sintered moulding procedures. The polymers can also be fabricated into films and other shaped articles and used in blends with other polymers for various applications such as adhesives.

Rokicki and Kuran, "*The Application of Carbon Dioxide as a Direct Material for Polymer Synthesis in Polymerization and Polycondensation Reactions*" *J. Macromol. Sci.-Rev. Macromol. Chem.*, C21(1), 135-136 (1981), present a survey of scientific literature on the use of carbon dioxide in polymerization and polycondensation reactions and describe, inter alia, the copolymerization of carbon dioxide with oxiranes using organozinc catalysts, such as diethylzinc-pyrogallol and zinc carboxylates as well as metallo-organic catalysts of cobalt, chromium, nickel, magnesium and aluminium, thereby indicating that a relatively large number of catalysts are active in promoting the copolymerization between carbon dioxide and oxiranes. Catalysts based on diethylzinc predominate in reports on the alternate copolymerization of carbon dioxide and oxiranes, but coordination catalysts, for example, metal carboxylates, have been less widely studied. Zinc derivatives, however, are said to exhibit higher activity than derivatives of cobalt or cadmium, while derivatives of aluminium, magnesium, chromium and nickel lead generally to low molecular weight polymers.

Soga, et al., *Polymer Journal*, 13, pages 407-410 (1981), disclose alternating copolymerization of carbon dioxide and propylene oxide with catalysts prepared from zinc hydroxide and dicarboxylic acids.

Soga, *Nippon Kagakkaishi*, Vol. 2, 295-300 (1982), investigates several types of catalyst systems which promote alternate copolymerization of carbon dioxide and alkylene oxides as possible improvements over the known catalyst system of diethylzinc and water. These alternate catalysts include metal oxide-supported diethylzinc, acetic acid salts of cobalt and zinc, reaction products of zinc hydroxide and dicarboxylic acids and metal oxide-supported zinc, cobalt and aluminium halides. The zinc dicarboxylate formed by reacting zinc hydroxide with glutaric acid was said to be about 3 times as active as the diethyl zinc.$H_2O$ system, but the catalyst prepared by reacting zinc oxide with glutaric acid was said to offer no improvement at all over the diethyl zinc.$H_2O$ system.

These prior art methods to synthetically prepare zinc glutarate (ZnGA) comprise mixing zinc oxide with glutaric acid in an organic solvent such as toluene or benzene at a certain temperature and for a certain time period. The glutaric acid dissolves in the organic solvent and reacts with ZnO suspended particles in solution to produce the catalyst (e.g. see Wang, S. J., et al., *Synthesis and Characterization of Alternating Copolymer from Carbon Dioxide and Propylene Oxide. Journal of Applied Polymer Science*, 2002. 85: p. 2327-2334). However, the major drawback in the preparation of ZnGA catalyst is the use of toxic, carcinogenic and flammable organic solvents like toluene or benzene.

It is an object of the present invention to overcome or ameliorate at least one of the disadvantages of the prior art, or to provide a useful alternative.

SUMMARY OF THE INVENTION

According to a first aspect the present invention provides a method for producing an organometallic catalyst, said method comprising the steps of:
  combining a polycarboxylic acid or anhydride and a metal-oxide, metal-hydroxide or metal-salt with a solvent at a temperature and pressure at which the solvent exists as a supercritical or near-critical fluid; and
  reacting said polycarboxylic acid or anhydride with said metal-oxide, metal-hydroxide or metal-salt for sufficient time and under sufficient temperature and pressure to produce said organometallic catalyst.

As used herein, the term 'near-critical' defines temperature and pressure conditions where a fluid is sufficiently hot and compressed that the distinction between the liquid and gaseous phases is almost non-existent. To explain, in any system containing liquid and gaseous phases, there exists a special combination of pressure and temperature, known as the critical point, at which the transition between liquid and gas becomes a second-order transition. Near the critical point, the fluid is sufficiently hot and compressed that there is substantially no distinction between the liquid and gaseous phases. It will be appreciated that the organometallic catalyst of the invention can be produced in a solvent at or above its critical point, or below its critical point in a subcritical or near-critical state. It will be appreciated that the terms 'dense gas' is used herein synonymously with the phrase 'supercritical or near-critical fluid'. For example a dense gas is considered a fluid at above its critical point or at conditions with a liquid like density. As an example, carbon dioxide is considered as a dense gas at 5° C. and 50 bar with a density of 904.5 g/mL, and 25° C. and 100 bar with a density of 813.9 g/mL.

Preferably the reaction is carried out at temperatures of between about 40% to 150% of the critical temperature and pressures of between about 40% to 150% of the critical pressure for any given solvent system. Preferably the temperature/pressure is chosen from 40, 50, 60, 70, 80, 90, 100, 110, 120, 130, 140, or 150% of the critical temperature/pressure.

In one embodiment, the solvent in its supercritical or near-critical state is in its supercritical state. In an alternative embodiment the solvent in its supercritical or near-critical state is below its supercritical state, in a subcritical state.

Preferably the solvent is free from toxic and/or carcinogenic and/or mutagenic and/or hazardous organic solvents such as toluene, benzene, xylene, acetone, methanol, chloroform, methylene chloride, dimethyl formamide, dimethyl sulfoxide, halogentated hydrocarbons, pyridine, ketones, aldehydes and alcohols.

Preferably the solvent utilised in the reaction to produce the organometallic material of the invention is relatively easily and completely removed from the reaction product. For example, where solvents such as toluene, xylene, benzene are used they will remain in the reaction product in trace amounts, whereas solvents such as $CO_2$ are evaporable and leave no trace residue. $CO_2$ is relatively inexpensive, readily available, inert, non-flammable, non-toxic, and its density is 'tunable' by changing by process temperature and pressure, thereby enabling a compound to be dissolved at high pressures and then separated by decreasing the pressure of the system. In contrast, the separation of an organic solvent from a product requires a further processing stage, and so it time consuming and adds cost. The residue of organic solvent is major issue for products which are used in foodstuffs and pharmaceutical products.

Preferably the solvent is carbon dioxide, ethylene, methane, nitrous oxide, refrigerants (such as R314), nitrogen, air, or water.

In another embodiment the solvent may comprise a liquid solvent in a subcritical state, which may be selected from the group consisting of methane, ethane, ethylene, propylene, trifluorochloromethane, difluoromethane, isomers of tetrafluoroethane, pentafluoroethane, isomers of trifluoroethane, isomers of pentafluoropropane, difluorochloromethane, isomers of tetrafluorochloroethane, carbon dioxide, nitrogen, ammonia, and mixtures of two or more thereof.

Any suitable solvent can be used for the present invention, however preferably the solvent is chosen from those which are low in odour, are environmentally friendly, have little or no toxicity and have little or no carcinogenicity. Preferably the solvent has reduced odour and/or carcinogenicity and/or toxicity compared to conventional solvents such as toluene, benzene, xylene, acetone, methanol, chloroform, methylene chloride, dimethyl formamide, dimethyl sulfoxide.

In one embodiment the polycarboxylic acid or anhydride is dissolved in the solvent to produce a solution, however in another embodiment the polycarboxylic acid or anhydride is suspended in the solvent to produce a suspension. It will be appreciated that the polycarboxylic acid or anhydride may be partially solubilised in the solvent.

According to a second aspect the present invention provides an organometallic catalyst or material when produced by the method according to the first aspect.

Preferably the metal of the metal-oxide, hydroxide or salt is selected from the group consisting of: zinc, cobalt, cadmium, chromium, nickel, magnesium, manganese, iron and aluminium. Preferably the metal-oxide is zinc oxide.

Preferably the polycarboxylic acid or anhydride is highly soluble in said solvent to produce said solution. As used herein the term polycarboxylic acid defines two or more carboxylic acid groups. Polycarboxylate acids or anhydrides can be selected from dicarboxylates, tricarboxylates tetracarboxylates or polymeric compounds with pendant carboxylate functions. Mixtures of polycarboxylic acids and anhydrides may be employed, as many compounds bear both anhydride and carboxylic acid functionalities.

Preferably the polycarboxylic acid is selected from the group consisting of: glutaric acid, 2,2-dimethylglutaric acid, 3,3-dimethylglutaric acid, 2-methylglutaric acid, 3-methylglutaric acid, 3-phenylglutaric acid, 2-ketoglutaric acid, 3-ketoglutaric acid, diglycolic acid, 3,3-tetramethyleneglutaric acid, adipic acid and mono-methyl glutarate. However, the skilled person will readily appreciate other polycarboxylic acids that will be useful in the present invention.

Preferably the polycarboxylic acid is glutaric acid.

Preferably the polycarboxylic anhydride is selected from the group consisting of: glutaric anhydride, 2,2-dimethylglutaric anhydride, 3,3-dimethylglutaric anhydride, 2-methylglutaric anhydride, 3-methylglutaric anhydride, 3-phenylglutaric anhydride, 2-ketoglutaric anhydride, adipic anhydride, 3-ketoglutaric anhydride, diglycolic acid, and 3,3-tetramethyleneglutaric anhydride. However, the skilled person will readily appreciate other polycarboxylic anhydrides that will be useful in the present invention.

Preferably the polycarboxylic acid or anhydride solution is reacted with the metal-oxide, hydroxide or salt for sufficient time and temperature and under sufficient pressure to produce the organometallic catalyst/material of the invention.

Alternatively the polycarboxylic acid may be in suitably protected forms, such as a nitrile or ester, in which case the reaction conditions will generally employ a deprotection step.

Preferably the reaction time is about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 hours. More preferably the reaction time is less than 6 hours.

Preferably the reaction temperature is about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, or 250° C. More preferably the reaction temperature is less than 60° C.

Preferably the reaction pressure is about 10, 20, 30, 40, 50, 60, 70, 80, 90, 100, 110, 120, 130, 140, 150, 160, 170, 180, 190, 200, 210, 220, 230, 240, 250, 260, 270, 280 or 300 bar. More preferably the reaction pressure is below 100 bar.

Any specific combination of time, temperature and pressure as outlined above is encompassed by the present invention.

According to a further aspect the present invention provides zinc glutarate when produced in a supercritical fluid or under supercritical fluid conditions, or in a near-critical fluid or under near-critical conditions. Preferably the present invention provides zinc glutarate when produced by combining and reacting a polycarboxylic acid or anhydride and a metal-oxide, hydroxide or salt in the presence of a solvent and at a temperature and pressure sufficient to cause the solvent to exist as a supercritical or near-critical fluid. The following scheme illustrates the production of ZnGA from ZnO and glutaric acid.

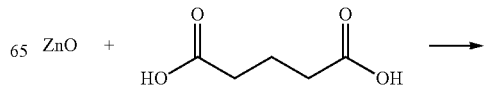

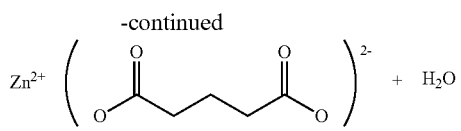

According to a third aspect the present invention provides a process for making a poly(alkylene carbonate) comprising contacting under copolymerization conditions carbon dioxide and one or more oxirane compounds in the presence of a catalytic amount of an organometallic catalyst produced by the method according to the first aspect. According to a further aspect the present invention provides poly(alkylene carbonate) when produced by the method according to the third aspect.

Preferably the oxirane (epoxide) compound is ethylene oxide or propylene oxide and said poly(alkylene carbonate) is an alternating copolymer of carbon dioxide with ethylene oxide or propylene oxide. The catalyst can also be used for the synthesis of other polymers such as polyesters (poly lactic acid), poly caprolactone and block co-polymers comprised of epoxide, caprolactone, etc. Cyclohexene oxide can also be catalysed by ZnGA to produce poly(cyclohexene carbonate), however higher reaction temperatures, such as 120° C., are required.

According to a fourth aspect the present invention provides use of the organometallic catalyst produced by the method according to the first aspect in a foodstuff or a pharmaceutical composition or as a thermal stabiliser for a polymer.

According to a fifth aspect the present invention provides a formulation for producing an organometallic catalyst, said formulation comprising: supercritical or near-critical $CO_2$, a polycarboxylic acid or anhydride and a metal-oxide, metal-hydroxide or metal-salt.

According to a sixth aspect the present invention provides an organometallic catalyst for forming polymer from monomer, comprising a metal selected from Zn, Co, Cr, Cd, Ni, Mg, Mn, Fe, Al and a polycarboxylic ligand, said catalyst having a catalytic activity of 80 g polymer produced per 1 g catalyst consumed. Preferably the polycarboxylic acid is selected from the group consisting of: glutaric acid, 2,2-dimethylglutaric acid, 3,3-dimethylglutaric acid, 2-methylglutaric acid, 3-methylglutaric acid, 3-phenylglutaric acid, 2-ketoglutaric acid, 3-ketoglutaric acid, diglycolic acid, 3,3-tetramethyleneglutaric acid, adipic acid and mono-methyl glutarate. However, the skilled person will readily appreciate other polycarboxylic acids that will be useful in the present invention.

According to a seventh aspect the present invention provides an organometallic catalyst when produced by the method of the invention having catalytic activity (turnover number) of at least 50 grams polymer produced per gram catalyst. Preferably the catalytic activity of the organometallic catalyst is greater than 20, 30, 40, 50, 60, 70, 80, 90, 100, 125, 150, 175, or 200 grams polymer produced per gram catalyst.

The turnover number is typically defined as the number of moles of substrate that a mole of catalyst can convert before becoming inactivated. The turnover frequency (which refers to the turnover per unit time) is also used to define catalyst activity. For zinc heterogeneous catalyst group, a turnover number from 3.9 up to 134 (moles of PO consumed per mole of zinc) and a turnover frequency from 0.06 up to 3.4 (moles of PO consumed per mole of zinc per hour) have been reported.

Preferably the particle size of the organometallic catalyst when produced by the method of the invention is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 micron.

Preferably the crystallinity of the organometallic catalyst when produced by the method of the invention is greater than about 50, 55, 60, 65, 70, 75, 80, 85, 90, 91, 92, 93, 94, 95, 96, 97, 98, or 99%.

Preferably the purity of the organometallic catalyst when produced by the method of the invention is greater than about 50, 55, 60, 65, 70, 75, 80, 85, 90, 91, 92, 93, 94, 95, 96, 97, 98, or 99%.

It has been surprisingly found that the use of supercritical or near-critical $CO_2$ to prepare ZnGA provides significant control over the crystallinity, and/or particle size and/or catalytic activity and/or surface area of the resultant organometallic catalytic material. This is in contrast to prior art methods of preparation which use toxic and flammable organic solvents, such as toluene. For example, whilst prior art methods of production produce partially crystalline material, the novel methods of the invention allow the production of partially or completely crystalline material. Importantly, the present invention allows the control over the crystallinity of the organometallic material by controlling the various reaction parameters. For example, the properties of the ZnGA produced by the methods of the invention are controllable by selectively varying the pressure of the reaction medium and/or the reaction time and/or the reaction temperature. The choice of supercritical fluid may affect the properties of the ZnGA produced by the invention. It has also been found that the catalytic activity of the ZnGA produced by the methods of the invention is relatively increased compared to ZnGA produced by prior art methods. Without wishing to be bound by any particular theory, it is believed that this is due to the control that the methods of the invention provide over the morphological structure of ZnGA, namely the Zn active site, crystallinity, crystal size and 'quality', and other catalyst parameters. It is also believed that the higher catalytic activity is provided by a larger surface area and smaller particle size.

As discussed in the foregoing, the most common method of synthesis of zinc glutarate (ZnGA), as taught in the prior art is to combine zinc oxide with glutaric acid in toluene at a certain temperature and for a time period. Glutaric acid dissolves in toluene and reacts with ZnO suspended particles in slurry solution to produce the catalyst. However, the ZnGA catalyst is produced in toxic, carcinogenic, and flammable organic solvents, such as toluene. The present inventors have ameliorated these issues by providing a synthetic pathway for the production of ZnGA which avoids the use of such organic solvents. Apart from the environmental benefits which follow from not using such organic solvents in the synthesis of ZnGA, the present invention enables ZnGA to be used as food or vitamin additives as-is, without the need for separate and complicated washing and purifications steps which remove trace toluene etc.

Preferably the reaction is stirred or agitated by mechanical, magnetic or ultrasonic stirring.

ZnGA is not only highly effective to catalyse the copolymerization of $CO_2$ and PO, but also very active for the synthesis of terpolymer poly(propylene carbonate-co-ε-caprolactone) and polyglycidol. The produced aliphatic polycarbonate has numerous potential applications in various areas of the polymer industry. For example, it may be used as a commodity polymer such as packaging material, as a biomedical polymer for tissue engineering or in drug delivery applications due to its biocompatibility, and as a temporary disposable binder since it completely thermally decomposes.

The present inventors also contemplate that the organometallic catalyst of the invention may be prepared in a reaction vessel, and then purified in the same reaction vessel, and then used in a polymerization reaction, which is also conducted in the same reaction vessel. The person skilled in the art would appreciate the advantages which result from having a '1-pot' process for synthesis of the organometallic catalyst and the subsequent polymerization of monomers using the synthesised organometallic catalyst.

$CO_2$ is regarded as one of the cheapest and most abundant carbon sources, but the relatively high thermal stability of $CO_2$ restricts its use as carbon raw material. This is one of the reasons that the copolymerization of $CO_2$ and alkylene oxides requires a highly active catalyst to initiate and accelerate the reaction. Among the heterogeneous catalyst systems reported to date, the catalytic activities of copolymerization of $CO_2$ with propylene oxide (PO) may be summarized and ranked as the following order: $Zn_3[Fe(CN)_6]_2$>ZnO/glutaric acid>Zn(OH)$_2$/glutaric acid>Mg-isoprene complex>Cr(OOCCH$_3$)$_3$>ZnO/adipic acid>ZnEt$_2$/pyrogallol>ZnEt$_2$/H$_2$O>ZnEt$_2$/poly(p-hydroxystyrene)>ZnEt$_2$/resorcinol. Whilst $Zn_3[Fe(CN)_6]_2$ displays the highest activity, its copolymer product contains a large fraction of ether linkages on the polymer backbone. So zinc glutarate synthesized from zinc oxide and glutaric acid is typically recognized as the most effective heterogeneous catalyst to deliver poly(alkylene carbonates) with a reasonably high molecular weight.

In one embodiment, the organometallic catalyst of the invention is produced according to the first aspect. However, in another embodiment a metal perchlorate hydrate is dissolved or suspended in a supercritical or near-critical solvent to produce a solution or a suspension, and is contacted with a dinitrile. The metal perchlorate and nitrile are then reacted for sufficient time and temperature and under sufficient pressure to produce the organometallic catalyst.

Preferably the metal perchlorate hydrate is a zinc perchlorate hexahydrate. Preferably the dinitrile is glutaronitrile.

In another embodiment the organometallic catalyst of the invention may be produced by reacting a metal alkyl compound with a polycarboxylic acid.

Preferably the polycarboxylic acid is selected from the group consisting of: glutaric acid, 2,2-dimethylglutaric acid, 3,3-dimethylglutaric acid, 2-methylglutaric acid, 3-methylglutaric acid, 3-phenylglutaric acid, 2-ketoglutaric acid, 3-ketoglutaric acid, diglycolic acid, 3,3-tetramethyleneglutaric acid, adipic acid and mono-methyl glutarate.

Preferably the polycarboxylic acid is glutaric acid.

Preferably the metal of the metal alkyl compound is selected from the group consisting of: zinc, cobalt, cadmium, chromium, nickel, magnesium and aluminium.

Preferably the metal alkyl compound is diethyl zinc.

In yet another embodiment, the organometallic catalyst of the invention may be produced by reacting a hydrated metal nitrate with a polycarboxylic anhydride.

Preferably the polycarboxylic anhydride is selected from the group consisting of: glutaric anhydride, 2,2-dimethylglutaric anhydride, 3,3-dimethylglutaric anhydride, 2-methylglutaric anhydride, 3-methylglutaric anhydride, 3-phenylglutaric anhydride, 2-ketoglutaric anhydride, adipic anhydride, 3-ketoglutaric anhydride, diglycolic anhydride, and 3,3-tetramethyleneglutaric anhydride.

Preferably the metal of the hydrated metal nitrate is selected from the group consisting of: zinc, cobalt, cadmium, chromium, nickel, magnesium and aluminium.

Preferably the hydrated metal nitrate is zinc nitrate hexahydrate.

In yet a further embodiment, the organometallic catalyst of the invention may be produced by reacting a metal oxide, chloride, perchlorate, nitrate or acetate with a dinitrile or a polycarboxylic acid. Preferably the dinitrile is glutaronitrile. Preferably the polycarboxylic acid is glutaric acid.

Carbon dioxide and one or more oxirane compounds can be copolymerized with coordination catalysts, such as zinc (II) carboxylates to provide poly(alkylene carbonates) having number average molecular weights of about $1 \times 10^4$ to $1.5 \times 10^5$ which correspond to weight average molecular weights of about $5 \times 10^4$ to $8 \times 10^5$. In general, these molecular weights vary with catalyst composition and preparation method.

The oxirane compounds used in the polymerization have the general structural formula:

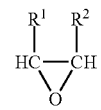

wherein $R^1$ is H, $CH_3$, $C_2H_5$, $C_3H_7$, $C_4H_9$, $C_6H_5$ or $C_6H_{11}$ and $R^2$ is H or $CH_3$.

Additionally, $R^1$ and $R^2$ together can complete a ring compound as illustrated by the broken line, wherein the ring may be a 3, 4, 5, 6, 7, or 8 membered ring.

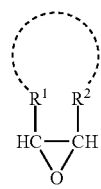

The polymerization reaction of $CO_2$ with the oxirane compounds results in a polymer having covalently linked alkylene carbonate units. In the case of copolymerization of carbon dioxide and propylene oxide, the more active catalysts tend to give higher molecular weight polymers of propylene carbonate. The molecular weight of these poly(propylene carbonates) appears to be insensitive to changes of other process parameters.

The catalyst which is used most effectively in this invention is a zinc dicarboxylate, which is the reaction product of a dicarboxylic acid or anhydride with zinc oxide, hydroxide or salt, such as zinc acetate or zinc carbonate. Preferably the catalyst is formed by using zinc oxide which is available commercially in consistent purities and reacting that compound with either glutaric acid or adipic acid. It is preferred to use an excess of zinc oxide, for example, about 2 to 5 mole % excess over the stoichiometric amounts required for the reaction.

The temperature of catalyst formation can vary from room temperature up to 50° C. for the initial reaction temperature, and the reaction usually occurs over a period of about 1 to 3 hours at 50° C. when using glutaric acid. The catalysts are produced as fine white powders that can be stored indefinitely under appropriate conditions.

According to an eighth aspect the present invention provides a method for controlling one or more crystal characteristics of an organometallic material during its synthesis, wherein said characteristics are selected from the group consisting of crystallinity, particle size, and porosity, said method comprising the steps of:

reacting a polycarboxylic acid or anhydride with a metal-oxide, metal-hydroxide or metal-salt in the presence of a solvent for sufficient time and under sufficient temperature and pressure to produce said organometallic catalyst, wherein said temperature and pressure are chosen to cause said solvent to exist either as a supercritical or a near-critical fluid, thereby controlling the crystal characteristics of the produced organometallic material.

According to a ninth aspect the present invention provides an organometallic material when produced or synthesized by the method according to the eighth aspect.

According to a tenth aspect the present invention provides a polymer or copolymer when prepared by a method using a catalyst of the present invention.

According to an eleventh aspect the present invention provides a method of producing a catalyst having a predetermined level of activity by controlling one or more crystal characteristics selected from the group consisting of crystallinity, particle size, and porosity, during formation under near-critical or supercritical conditions.

The skilled person will appreciate that the crystal characteristics may also be selected from crystal size, shape, and polymorphism.

The skilled addressee will understand that the invention comprises the embodiments and features disclosed herein as well as all combinations and/or permutations of the disclosed embodiments and features.

BRIEF DESCRIPTION OF THE DRAWINGS

Preferred embodiments of the invention will now be described, by way of example only, with reference to the accompanying drawings in which.

DEFINITIONS

Figure 1:
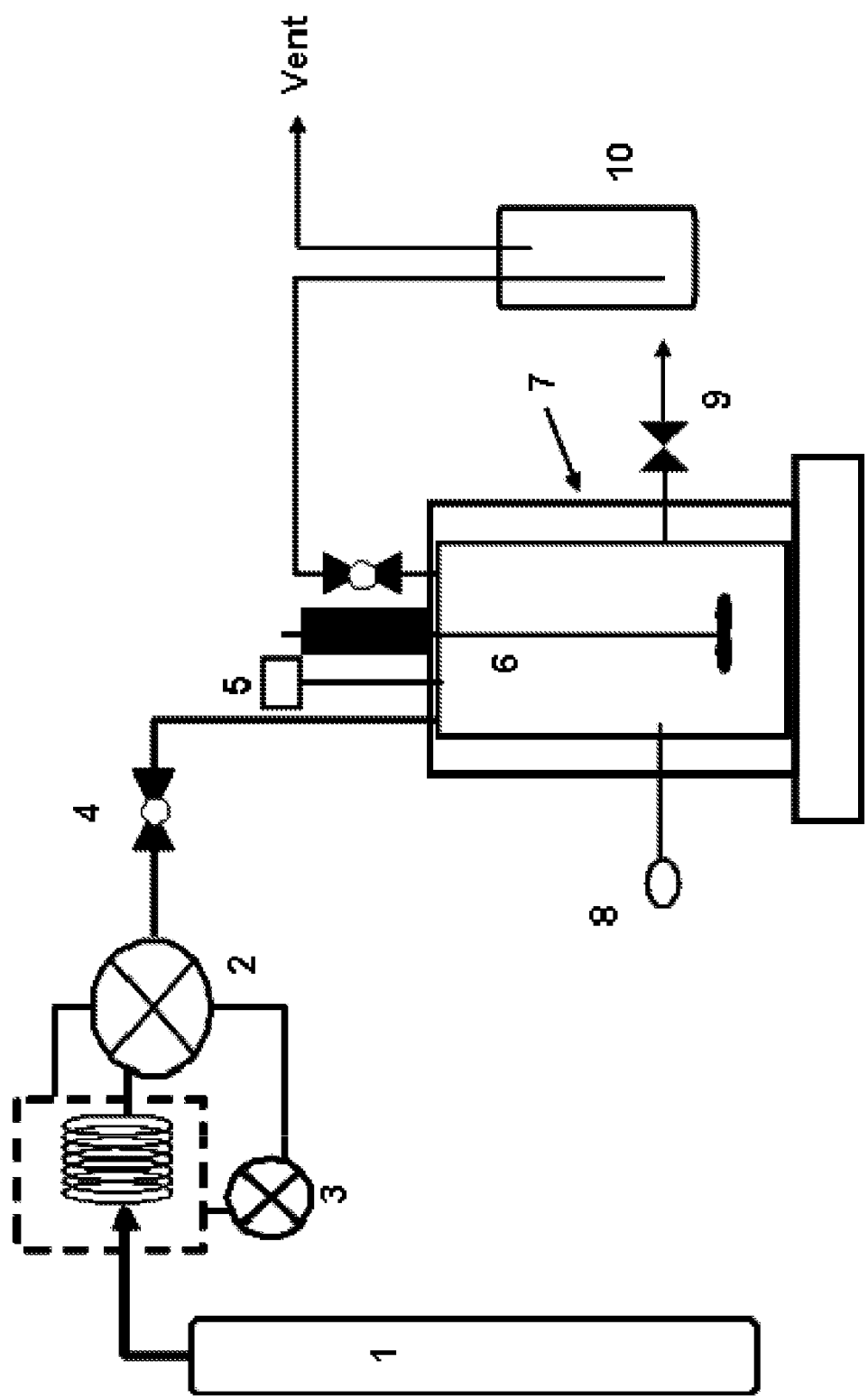
FIG. 1 is a schematic diagram of apparatus used for the synthesis of organometallic catalyst (ZnGA) under super-critical fluid conditions and for polymerization reactions, wherein (1) is a $CO_2$ cylinder, (2) is a high pressure pump, (3) is a recirculation pump, (4) is a valve, (5) is a pressure indicator, (6) is a stirrer, (7) is a reactor with a heating jacket, (8) is a thermocouple, (9) are pressure relief valves and (10) is a waste trap.

In describing and claiming the present invention, the following terminology will be used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

Headings of sections provided in this patent application and the title of this patent application are for convenience only, and are not to be taken as limiting the disclosure in any way.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

Other than in the operating examples, or where otherwise indicated, all numbers expressing quantities of ingredients or reaction conditions used herein are to be understood as modified in all instances by the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The examples are not intended to limit the scope of the invention. In what follows, or where otherwise indicated, "%" will mean "weight %", "ratio" will mean "weight ratio" and "parts" will mean "weight parts".

The recitation of a numerical range using endpoints includes all numbers subsumed within that range (e.g., 1 to 5 includes 1, 1.5, 2, 2.75, 3, 3.80, 4, 5, etc.).

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

PREFERRED EMBODIMENT OF THE INVENTION

Numerous embodiments are described in this patent application, and are presented for illustrative purposes only. The described embodiments are not intended to be limiting in any sense. The invention is widely applicable to numerous embodiments, as is readily apparent from the disclosure herein. These embodiments are described in sufficient detail to enable those skilled in the art to practice the invention, and it is to be understood that other embodiments may be utilized and that other changes may be made without departing from the scope of the present invention. Accordingly, those skilled in the art will recognize that the present invention may be practiced with various modifications and alterations. Although particular features of the present invention may be described with reference to one or more particular embodiments or figures that form a part of the present disclosure, and in which are shown, by way of illustration, specific embodiments of the invention, it should be understood that such features are not limited to usage in the one or more particular embodiments or figures with reference to which they are described. The present disclosure is thus neither a literal description of all embodiments of the invention nor a listing of features of the invention that must be present in all embodiments.

The present invention will now be described with reference to the following examples which should be considered in all respects as illustrative and non-restrictive.

Materials

Zinc oxide (ZnO) nanopowder and glutaric acid (GA) with purity 99% were purchased from Aldrich. Before reaction, glutaric acid was ground up to a fine powder. Food grade carbon dioxide (>99.9% purity) was obtained from BOC Company. The solvents used were all analytical grades. Toluene, methanol, dichloromethane were supplied by Aldrich, and acetone and absolute ethanol were purchased from Ajax Finechem and Merck chemical company, respectively. Propylene oxide (PO) with 99.5% purity was obtained from Fluka. Adipic acid (AA), 2-methyl glutaric acid (2-MGA), cobalt acetate (Co(OAc)$_2$) and benzoic acid (BA) were purchased from Sigma company.

Preparation of Catalysts

A schematic of the apparatus utilised for the synthesis of organometallic catalyst and polymer is presented in FIG. 1. The required amounts of the reactants e.g. zinc oxide and glutaric acid were added into the high pressure reactor 7 (ground GA (0.33 g, 2.5 mmol) and ZnO (0.202 g, 2.5 mmol)). The reactor was then assembled and the temperature of the vessel was adjusted to a desired value. The system was isolated by closing inlet and outlet valves, after which a high pressure pump (2, Thar Model 50P) was used to gradually pressurize the system. Prior to pressurization the air was purged from the system by opening exit valve at low pressures, such as 5 bar. After stirring the system 6 for a predetermined period of time the stirrer was stopped and then the vessel was slowly depressurized. The powder was collected and purified by washing with acetone, followed by washing with water and ethanol. The product was dried at room temperature under vacuum for 24 hours and stored in a desiccator for further characterisation. Other catalysts prepared from the reaction between ZnO and AA, 2-MGA, cobalt acetate and benzoic acid were also obtained with the process of the invention.

For comparison purposes, ZnGA was also prepared according to a conventional method as described in literature [Meng, Y. Z., et al., Effects of the Structure and Morphology of Zinc Glutarate on the Fixation of Carbon Dioxide into Polymer, J. Polym. Sci.: Part A: Poly. Chem., 2002. 40: p. 3579-3591]. Equal molar ratios of ZnO (4.05 g, 50 mmol) and GA (6.60 g, 50 mmol) were added into 150 mL toluene at 60° C., the mixture was stirred for 4 hours, and then the product was collected, followed by washing with acetone, water and ethanol then drying under the vacuum.

Characterisation

Catalyst

FTIR spectra of the catalysts were collected at a resolution of 4 cm$^{-1}$ and co-added 32 scans with an Attenuated Total Reflectance—Fourier Transform Infrared (ATR-FTIR) spectrometer (Varian 660-IR) over the range of 4000-550 cm$^{-1}$. The particle size and distribution of the catalysts suspended in chloroform were determined using Malvern Mastersizer 2000. Surface area, pore volume and pore size distribution were measured by the Brunauer-Emmet-Teller (BET) technique using a Quantachrome Autosorb-1 analyzer using nitrogen as an absorbing gas. Thermal behaviour of the catalysts was examined with thermogravimetric analysis (TGA) conducted with thermogravimetric analyser (SDT Q600) at ramping rate 20° C./min under nitrogen from 20° C. to 600° C. The crystallinity and crystal structure was measured by wide-angle X-ray diffraction (WXRD) with step size of 0.02° over the range of 4-90° were performed using a Siemens D5000 diffractometer with copper (Cu) k-alpha radiation with a wavelength of 1.5418 Angstroms. Field Emission Scanning Electron Microscopy (FE-SEM) was used to observe the surface morphologies of the catalysts. The samples were coated with gold and imaged with a Zeiss Ultra Plus field emission scanning electron microscope.

Synthesis and Characterisation of Poly(Propylene Carbonate)

The catalyst activity was measured for the synthesis of poly(propylene carbonate). Prior to the polymerisation reaction, ZnGA and the reactor were dried at 100° C. under vacuum to remove traces of water. A known amount of PO was then added into the vessel, the reactor was purged with CO$_2$ before heating and then pressurised with CO$_2$ up to the desired pressure at a predetermined temperature. After the set period of time the heater and stirrer 6 were turned off, the system was cooled down to room temperature and the pressure was slowly released. The polymer was collected and the catalyst was then removed from the product. The resulting polymer product was dissolved in dichloromethane (DCM) and the catalyst was extracted with dilute hydrochloric acid (5%). The mixture was then transferred to a separating funnel to remove the acid solution. The extraction process was repeated three times and followed by washing with distilled water. The final DCM solution was concentrated by using a rotary evaporator and the PPC product was precipitated by pouring the copolymer solution into methanol. The precipitated product was filtered and dried under vacuum at room temperature and the gross yield of polymer was measured by gravimetric method. Subsequently, the filtrate was evaporated to remove methanol and DCM to collect the copolymerisation by products that were soluble in methanol. The chemical structure of polymer chain was determined with Nuclear Magnetic Resonance (NMR) spectroscopic measurement by using a Bruker NMR spectrometer (DPX 400). Chloroform-d1 (CDCl$_3$) was used as the solvent.

Results

Synthesis of ZnGA

Figure 2A:
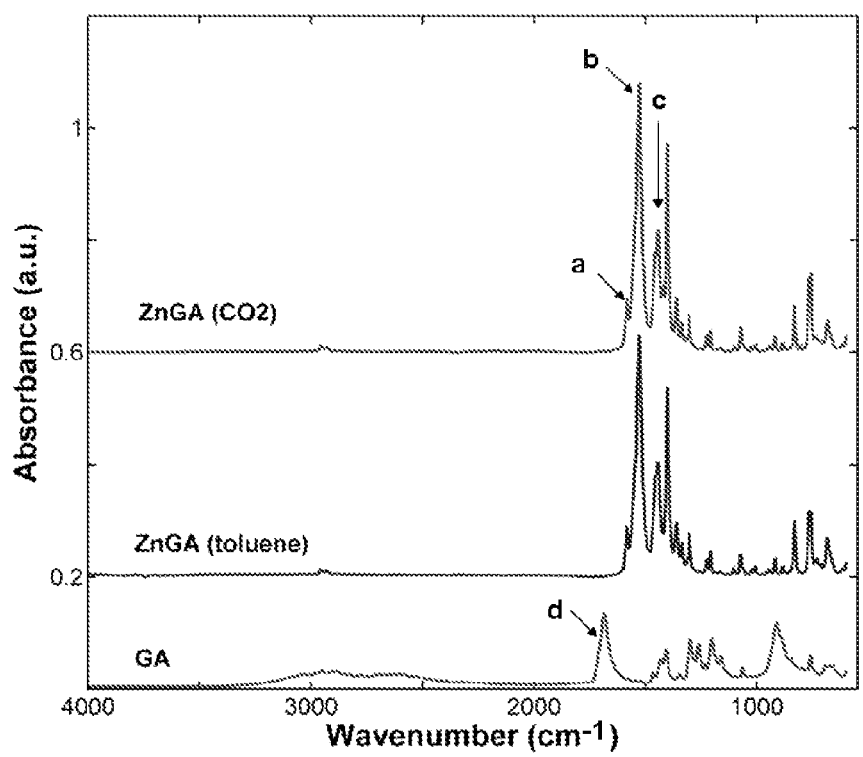
FIG. 2A are FTIR spectra of ZnGA synthesized in toluene (60° C., 4 hrs) and $CO_2$ system (60° C., 50 bar, 4 hrs). Peak a-c represents the zinc-carboxylate bond (COO—) absorbance at 1,585 $cm^{-1}$, 1,536 $cm^{-1}$ and 1,405 $cm^{-1}$ respectively, peak d represents the carbonyl (C=O) stretching of 1,697 $cm^{-1}$.

The FTIR spectra of ZnGA catalysts produced at 60° C. and 4 hours is shown in FIG. 2A. The FTIR spectra of ZnGA catalysts produced at high pressure are consistent with those reported in the literature for ZnGA prepared by conventional means. The absence of peak at 1,697 cm$^{-1}$ (peak d) and presence of peaks at 1,585 cm$^1$, 1,536 cm$^{-1}$ and 1,405 cm$^{-1}$ (peak a-c) corroborates that the GA carbonyl (C=O) group converted to zinc-carboxylate bond (COO—). These results confirm that the chemical structure of ZnGA produced from these two methods is identical. In addition, vibrational characteristic peak of GA, which is carbonyl (C=O) stretching of 1,697 cm$^{-1}$ was not detected in the FTIR spectrum, indicating no residual GA in the final product after purification.

Figure 2B:
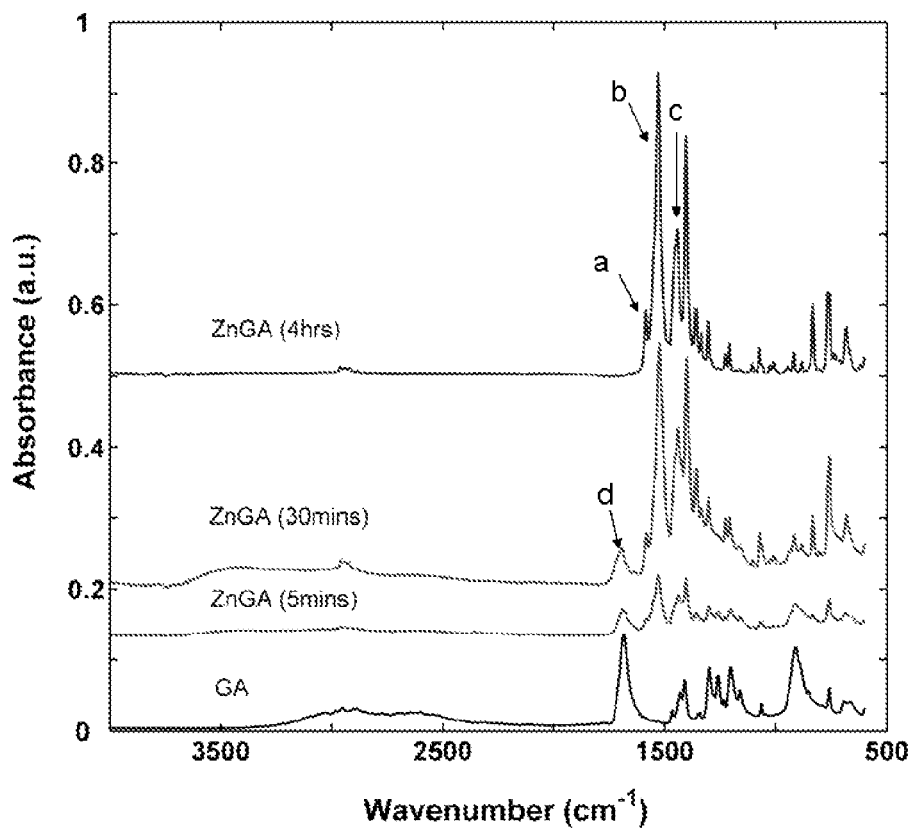
FIG. 2B are FTIR spectra of ZnGA synthesized in $CO_2$ system at 60° C., 50 bar. Peak a-c represents the zinc-carboxylate bond (COO—) absorbance at 1,585 $cm^{-1}$, 1,536 $cm^{-1}$ and 1,405 $cm^{-1}$ respectively, peak d represents the carbonyl (C=O) stretching of 1,697 $cm^{-1}$.

FTIR results in FIG. 2B show the effect of reaction time on the yield of the reaction. The peaks at 1,585 cm$^{-1}$, 1,536 cm$^{-1}$ and 1,405 cm$^{-1}$ reveal that zinc-carboxylate bond was formed even after 5 minutes. However, the peak at 1,697 cm$^{-1}$ confirms the presence of glutaric acid residue in the product and low yield of the reaction, when reaction carried out at 30 minutes. After four hours the peak for GA is absent in the FTIR spectrum of the catalyst produced at 60° C. and 50 bar.

The Effect of Reaction Time in High Pressure $CO_2$

Figure 3:
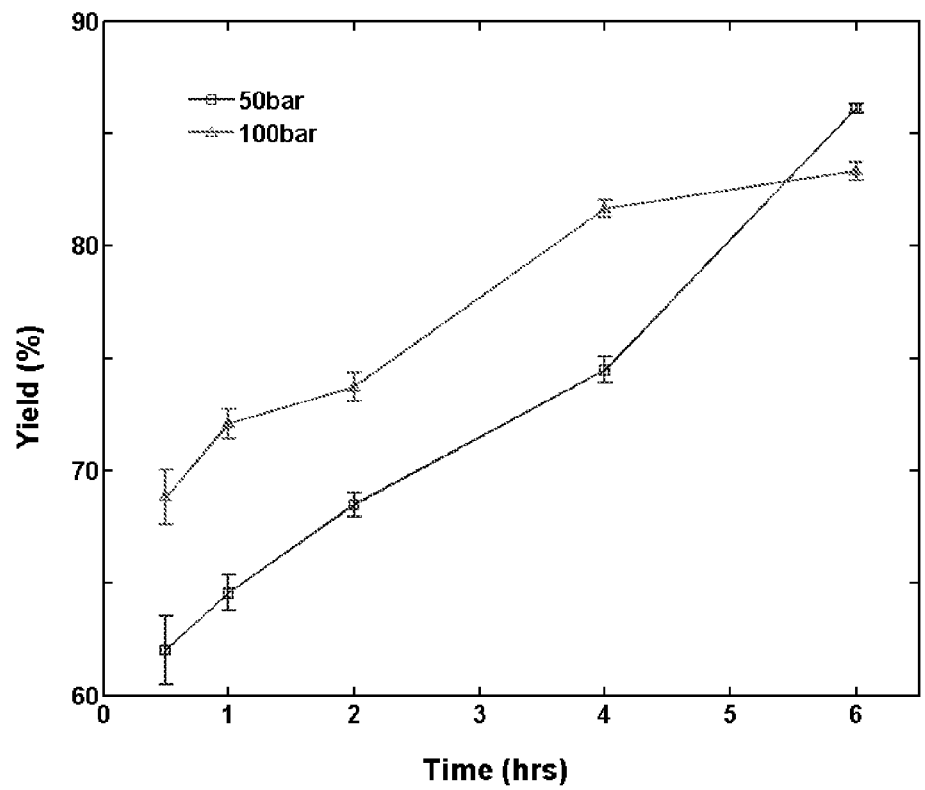
FIG. 3 is a graph showing the effect of reaction time on the yield of ZnGA at 60° C.

The effect of reaction time on the yield of ZnGA prepared under high pressure $CO_2$ was investigated. At subcritical $CO_2$ conditions, namely 50 bar and 60° C., the yield was enhanced considerably from 62% to 75% when the reaction time was increased from 30 minutes to 4 hours, as shown in FIG. 3. The reaction rate was substantially enhanced, when supercritical $CO_2$ was used; the yield increased from 68% to 82%, when the reaction time was increased from 30 minutes to 4 hours. However, the yield was slightly increased between four to six hours. The enhanced rate of reaction may result from increasing the solubility of GA in $CO_2$ at supercritical conditions compared with subcritical.

Effect of Pressure

Figure 4:
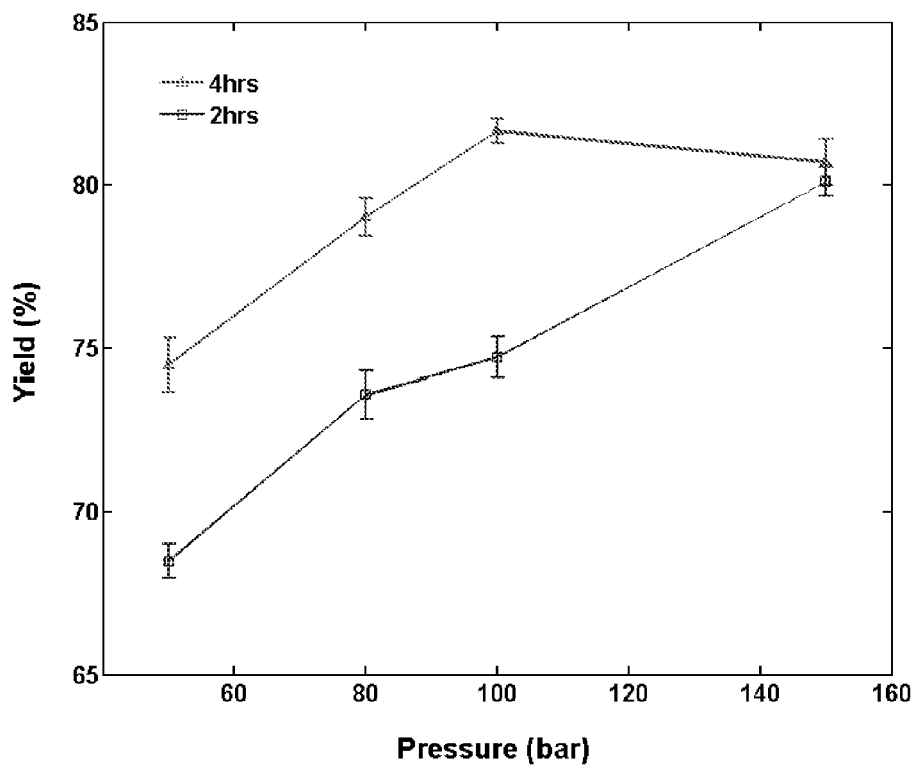
FIG. 4 is a graph showing the effect of pressure on the yield of ZnGA at 60° C.

As shown in FIG. 4, the yield of ZnGA was increased by increasing the reaction pressure. After 2 hours, the yield was 68% at 50 bar and increased to 80%, when the pressure approached 150 bar. However, the yield at 150 bar for both two hours and four hours was the same, indicating that at higher pressures, such as 150 bar, high yield are possible with shorter reaction times.

Effect of Reaction Temperature

Figure 5:
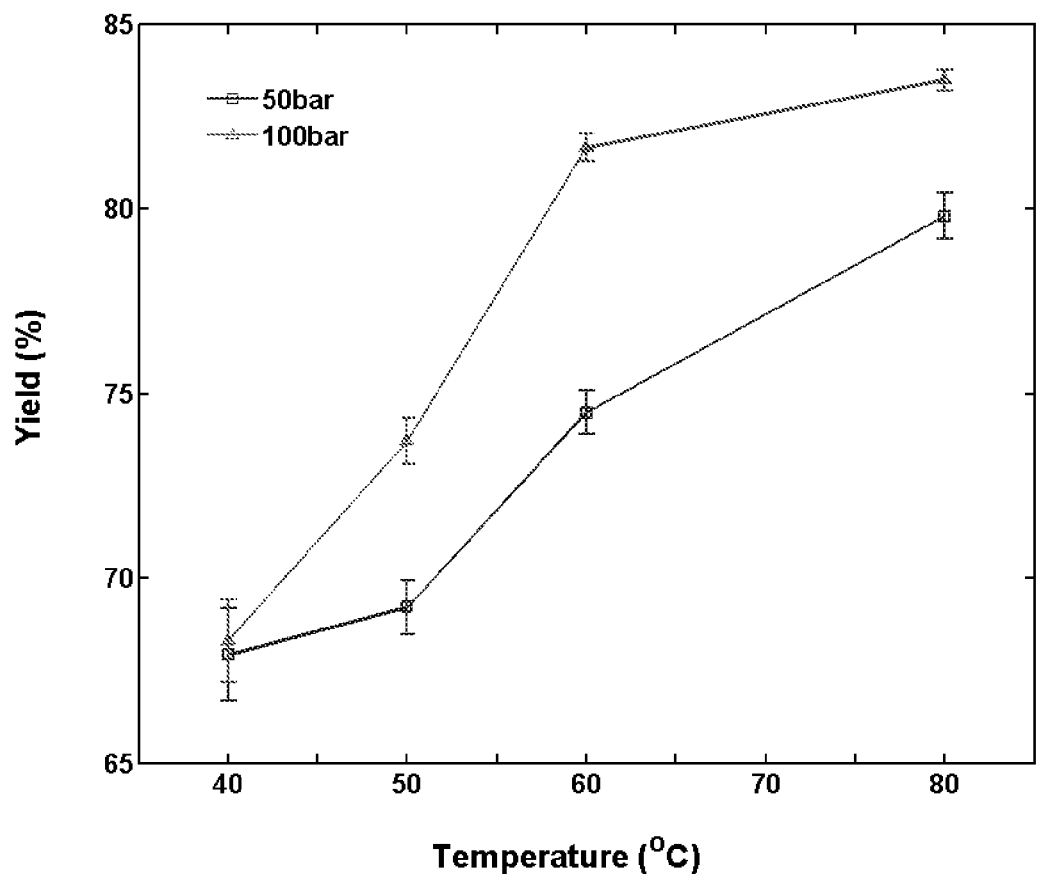
FIG. 5 is a graph showing the effect of temperature on the yield of ZnGA for 4 hrs.

Experiments were performed to determine the effect of temperature on the yield of ZnGA in $CO_2$. As shown in FIG. 5, at each pressure the yield was increased by raising the temperature, with the effect of temperature on the yield of ZnGA being more pronounced at 100 bar than 50 bar. Therefore, higher yields are possible at lower pressures by increasing the reaction time and also using higher operating temperatures.

By comparison with prior art methods, the optimum yield of ZnGA in toluene is about 95% at 60° C. and with a 4 hour reaction time, however under near-critical or supercritical $CO_2$ conditions the maximum yield was found to be 86%. Whilst the yield is lower under near-critical or supercritical conditions, the advantage is that a non-hazardous solvent can be employed. The solubility of the reactants in the solvent is a key factor in reaction and the final yield, wherein higher solubility will increase the yield of the reaction. The solubility of reactants in solvents is governed by their polarity, molecular weight, and the solvent density and physical properties. The solvation power of a solvent is higher than a gas due to higher density. The solvation power of a supercritical fluid can be 'tuned' over a wide range by tailoring the pressure and/or temperature of the system. Whilst zinc oxide is insoluble in toluene and $CO_2$, GA is soluble and the concentration of GA in the reaction medium is important for the reaction to take place. The density of $CO_2$ increases with increasing pressure from 50 bar to 150 bar, and so the solubility of GA is increased as the pressure increases. The higher solubility of GA in $CO_2$ at higher pressures is likely to be responsible for improved yields even at shorter reaction times, due to increased mass transfer properties in supercritical $CO_2$ compared to common organic solvents.

ZnGA was synthetically prepared at 60° C. and at both different pressures and reaction times to assess the effect of process variables on the properties of the catalysts, as shown in Table 1.

TABLE 1

ZnGA prepared under different reaction conditions.

| ZnGA | Cat. T | Cat. 1 | Cat. 2 | Cat. 3 | Cat. 4 |
|---|---|---|---|---|---|
| Pressure (bar) | In toluene | 50 | 50 | 100 | 150 |
| Reaction time (hrs) | 4 hrs | 4 | 6 | 4 | 2 |
| Yield (%) | 95.38 | 74.49 | 86.10 | 81.66 | 80.10 |

ZnGA produced in toluene obtained the best yield of 95.38%. However, from the subcritical $CO_2$ synthesis a yield of 86.10% was obtained by reacting the reactants for 6 hours at 50 bar, which is a comparable yield to the conventional synthesis. When the reaction was conducted at supercritical condition (100 and 150 bar, 60° C.), the yield was around 80% after only 2 hours. It is contemplated that the unique properties of the supercritical solvent, including liquid-like density and gas-like diffusibility with low surface tension, enhance the heat and mass transfer during the reaction, and as a consequence improves the nucleation making the synthesis of the catalyst relatively fast.

Crystallinity of ZnGA Catalysts

An XRD analysis can be used to determine the degree of crystallinity of catalyst and the presence of unreacted ZnO, which can influence the catalyst's activity. Whilst any unreacted glutaric acid residue can be relatively easily washed away by acetone and water, it is not practical to remove ZnO residues easily.

Figure 6A:
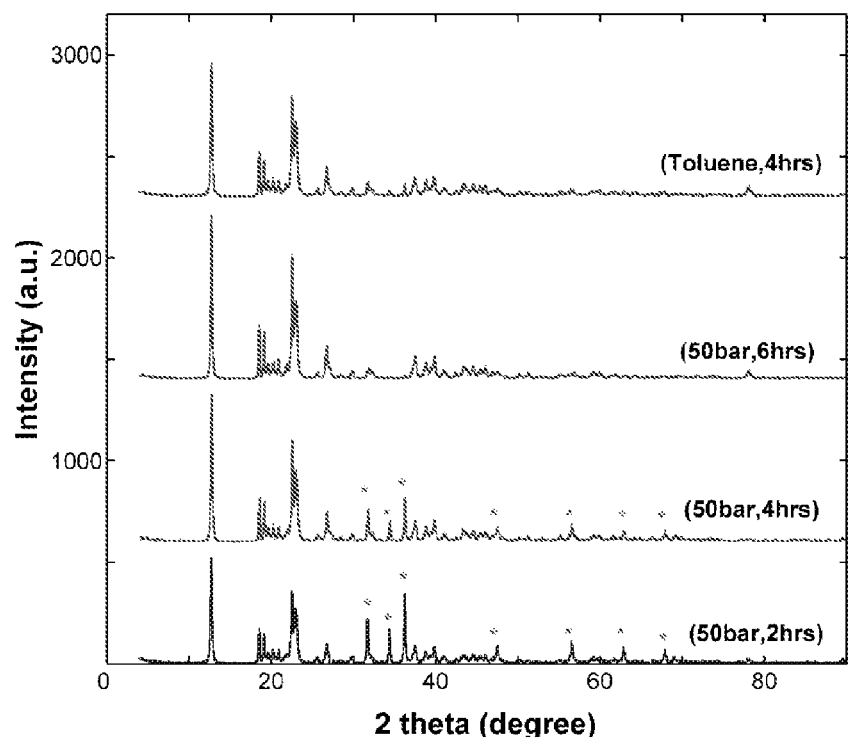
FIGS. 6A and B are XRD patterns showing the effect of reaction time (a) and pressure (b) on the XRD patterns of ZnGA synthesized at 60° C. (a,b,c are the major peaks for the ZnGA and asterisks are the characteristic peaks of zinc oxide)

The crystal structure of ZnGA synthesized from conventional methods and under the method of the invention was determined by WXRD; the diffraction patterns are shown in FIG. 6. At all conditions examined, the WXRD profiles of ZnGA were the same, indicating that the crystal lattice structure was not a function of reaction conditions.

Figure 6B:
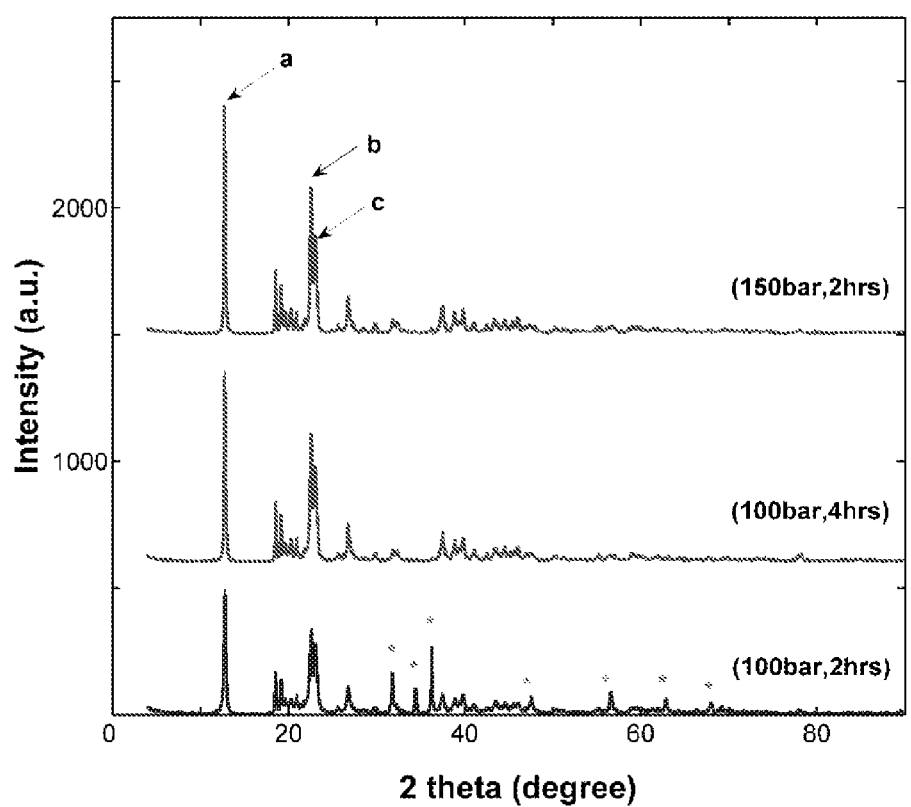

Low intensity peaks that were typical for presence of zinc oxide residues were observed in the WXRD pattern of batches prepared under subcritical or supercritical $CO_2$ at relatively short reaction times, such as 2 hrs at 50 bar and 100 bar. The results in FIG. 6A suggest that at lower pressures, longer reaction times are necessary to achieve high yield and minimize the amount of ZnO residue. In contrast, ZnO residues were negligible when the reaction was conducted at 50 bar for 6 hrs and 100 bar for 4 hrs. However, at high pressure such as 150 bar, the residue of unreacted zinc oxide was low even after 2 hrs due to relatively faster reaction rates (FIG. 6B).

According to the Scherrer Equation (below), higher crystallinity and improved crystal 'quality' (comprising crystallite size and 'perfectness') lead to sharper peaks and higher intensities. The differences of peak intensities and broadness levels observed in WXRD patterns directly reflect that the catalyst crystallinity and crystal quality are dependent upon the reaction conditions used for the synthesis. The peaks on WXRD pattern of ZnGA fabricated at 50 bar (peaks a, b, c in FIG. 6) were sharper and more intense for a 6 hr reaction time compared to a 2 hr reaction time. At a 2 hr reaction time the peak intensities were increased by increasing pressure from 100 bar to 150 bar.

$$\beta = \frac{K\lambda}{L\cos\theta}$$

β is the line broadening at half the maximum intensity (FWHM) in radians, K is a constant that varies with the method of taking the breadth (0.89<K<1), λ is the wavelength of incident x-rays, typically 1.54 Å, θ is the Bragg angle, and L is the mean crystallite dimension. An interactive curve-fitting technique was applied to analyze the WXRD profiles. The overall crystallinity (Xc) was estimated with the deconvoluted crystalline and amorphous peaks of each catalyst. The coherent length (Lc) of crystallite was calculated from its full width at half-maximum with the Scherrer equation. Three strong peaks (peak a-c) were selected to estimate the crystallite size and the overall crystallinity was determined from the WXRD patterns.

WXRD results of ZnGA catalysts synthesized under near-critical and supercritical conditions were compared with the catalyst produced in toluene (See Table 2). The crystallite mean dimension (Lc), a reference that relies on crystal quality, was determined to be a function of diffraction peaks and the Bragg angles. Lc values of ZnGA synthesized in $CO_2$ (Cat. 1-4) are higher than the catalyst synthetically prepared in toluene (Cat. T). This result demonstrates that utilising $CO_2$ in the reaction surprisingly promoted the crystal quality of the catalyst. The overall crystallinity (Xc) was generally higher for catalyst synthetically prepared in high pressure $CO_2$ compared with the catalyst prepared in toluene. The lower crystallinity of ZnGA produced at 50 bar for 4 hrs (Cat. 1) was due to unreacted ZnO that was present as impurity in the product. In general, it is contemplated that the degree of ZnGA crystallinity is enhancable by 10% when prepared by the method of the invention compared with toluene as a reaction medium. Since the rate of reaction is faster at higher pressures, it is possible to achieve a higher degree of crystallinity at a shorter reaction time by utilising the methods of the invention.

It is contemplated that the morphological structure of ZnGA, including the degree of crystallinity, crystal size and shape affect the catalytic activity of the organometallic catalysts of the invention. For example, it has been discovered that the ZnGA catalysts with higher crystallinity exhibit higher catalytic activity in the copolymerisation of $CO_2$ with oxirane.

Morphologies of ZnGA Catalysts

Figure 7:
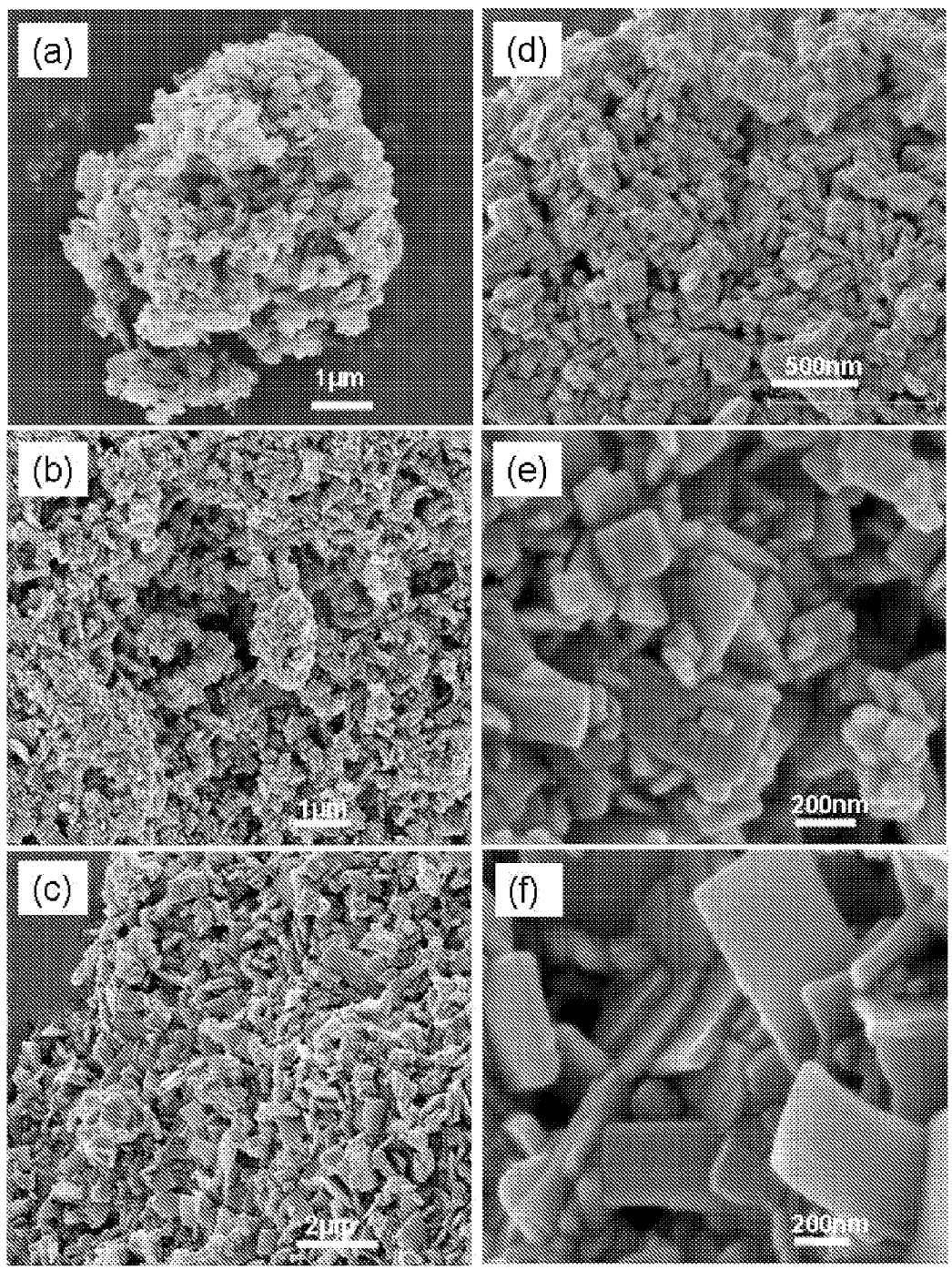
FIG. 7 shows SEM images of ZnGA synthesized at 60° C. (a) Cat. 3 ($CO_2$ 100 bar 4 hrs); (b) Cat. T (toluene, 4 hrs); (c) Cat. 4 ($CO_2$ 150 bar 2 hrs); (d) Cat. 2 ($CO_2$ 50 bar 4 hrs); (e) Cat. T (toluene, 4 hrs); (f) Cat. 4 ($CO_2$ 150 bar 2 hrs)

The results of the field emission SEM are shown in FIG. 7, which shows that ZnGA catalysts have the form of aggregated small rectangular plate crystals. This rectangular morphology is similar as the single-crystal ZnGA crystals synthesized via the hydrothermal reactions of zinc perchlorate hexahydrate and glutaronitrile reported in the literature. The catalyst synthesized in toluene (FIG. 7b) comprises a more porous structure compared with those produced under near critical or supercritical $CO_2$ (see FIGS. 7(c), (d) and (f) at higher magnifications). The crystallite size affects the overall crystallinity, namely, highly crystalline catalyst (Cat. 4, 91.9% crystallinity) was formed with significantly larger sized and more regularly shaped crystals, compared with Cat. 1 and Cat. 2 which each have lower degrees of crystallinity (shown in FIG. 7(f), (d) and (e)).

Particle Size and Surface Area of ZnGA Catalysts

Figure 8:
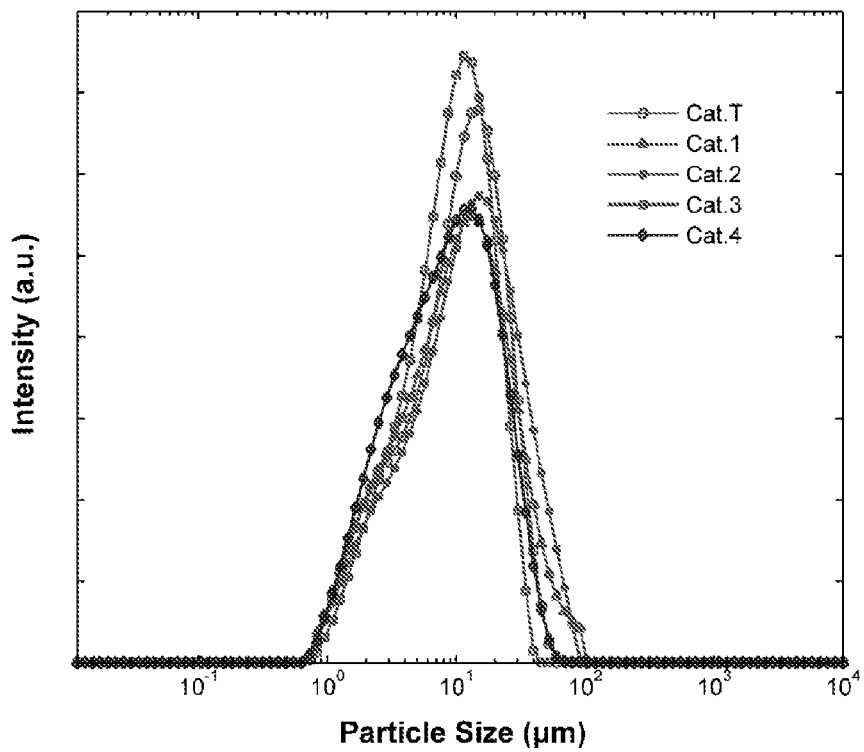
FIG. 8 is a graph showing particle size distributions of ZnGA catalyst synthesized in toluene (Cat. T), in $CO_2$ system with 50 bar 4 hrs (Cat. 1), 50 bar 6 hrs (Cat. 2), 100 bar 4 hrs (Cat. 3) and 150 bar 2 hrs (Cat. 4) (all the catalysts were produced at 60° C.)
Figure 9:
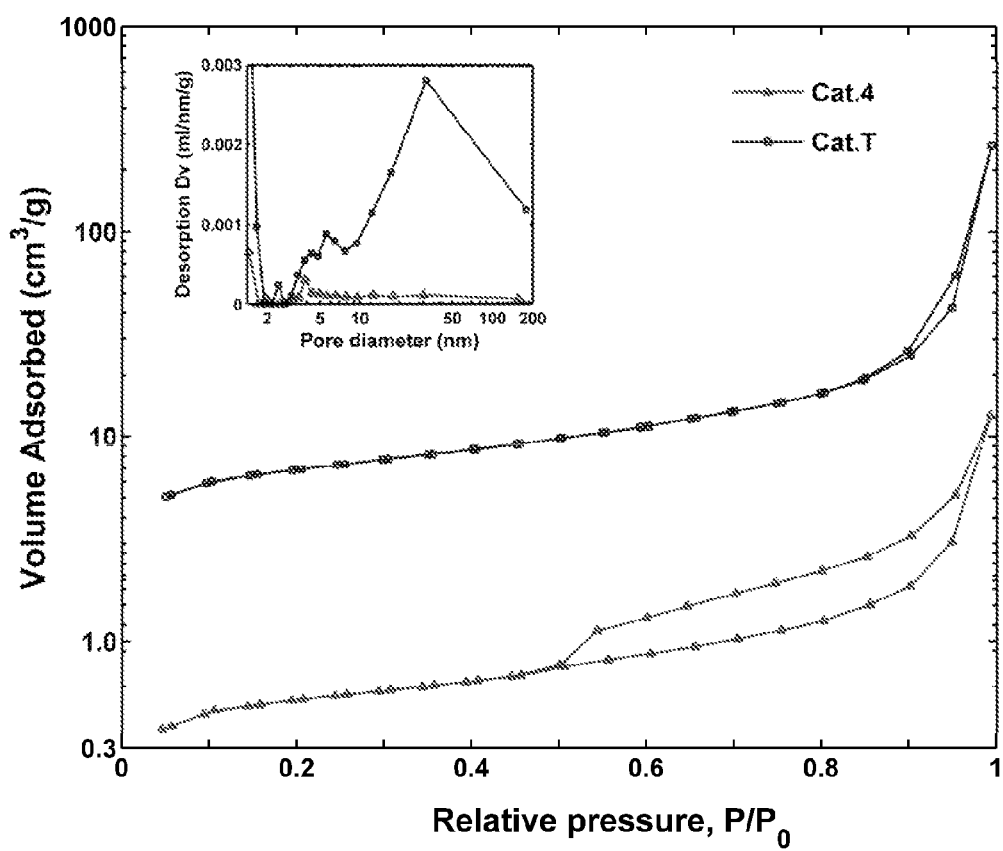
FIG. 9 shows $N_2$ adsorption/desorption isotherms of Cat. 4 and Cat. T.

The catalytic activity of heterogeneous catalyst is mainly a function of particle size, surface area and crystallinity. It was found that particle sizes larger than 20 μm were achievable when using distilled water wash followed by oven drying, and that washing the catalyst using ethanol followed by vacuum drying at room temperature significantly decreased the particle size of the catalysts to 5 μm. The average particle sizes of the catalysts prepared in both $CO_2$ and toluene were within the range of 4 μm to 6 μm regardless of the synthesis conditions (Table 3). Compared with synthesis in toluene (which is conducted at atmospheric pressure), the particle size was slightly lower when high pressure $CO_2$ was used. The results in Table 3 and FIG. 8 demonstrate that by controlling the purification procedure, the particle size and also distribution were similar between the different synthesis methods.

TABLE 2

WXRD results of ZnGA catalysts obtained at 60° C.

| WXRD | ZnGA | | | | |
|---|---|---|---|---|---|
| | Cat. T (toluene, 4 hrs) | Cat. 1 (50 bar, 4 hrs) | Cat. 2 (50 bar, 6 hrs) | Cat. 3 (100 bar, 4 hrs) | Cat. 4 (150 bar, 2 hrs) |
| Peak a | | | | | |
| 2θ (°) | 12.70 | 12.74 | 12.72 | 12.74 | 12.72 |
| FWHM (°) | 0.26 | 0.24 | 0.23 | 0.23 | 0.22 |
| Lc (Å)* | 332 | 363 | 387 | 385 | 411 |
| Peak b | | | | | |
| 2θ (°) | 22.52 | 22.56 | 22.52 | 22.54 | 22.54 |
| FWHM (°) | 0.34 | 0.32 | 0.31 | 0.35 | 0.30 |
| Lc (Å) | 245 | 264 | 273 | 241 | 288 |
| Peak c | | | | | |
| 2θ (°) | 22.96 | 23.00 | 23.00 | 23.00 | 23.02 |
| FWHM (°) | 0.46 | 0.42 | 0.42 | 0.44 | 0.40 |
| Lc (Å) | 180 | 196 | 199 | 189 | 206 |
| Xc (%)** | 82.6 | 78.1 | 85.9 | 92.0 | 91.9 |

*The mean crystallite dimension (Lc) is estimated according to the Scherrer Equation.
**The overall crstallinity (Xc) is estimated from the crystalline peaks and amorphous peaks deconvoluted for a WXRD profile.

TABLE 3

Particle sizes and surface areas of the ZnGA catalysts prepared at 60° C.

| ZnGA | Particle size (μm) | Polydispersity $(D_{90} - D_{10})/D_{50}$ | Surface area (m²/g) |
|---|---|---|---|
| Cat. T (toluene, 4 hrs) | 5.61 ± 0.12 | 2.36 ± 0.13 | 22.05 ± 0.18 |
| Cat. 1 (50 bar, 4 hrs) | 5.98 ± 0.02 | 2.83 ± 0.09 | 12.05 ± 0.11 |
| Cat. 2 (50 bar, 6 hrs) | 5.38 ± 0.07 | 3.20 ± 0.19 | 11.92 ± 0.10 |
| Cat. 3 (100 bar, 4 hrs) | 4.90 ± 0.16 | 2.76 ± 0.16 | 13.63 ± 0.12 |
| Cat. 4 (150 bar, 2 hrs) | 4.76 ± 0.04 | 2.67 ± 0.17 | 12.01 ± 0.11 |

The surface area of the ZnGA catalyst prepared in toluene (ZnGA-T) and at pressurised $CO_2$ was 22.05 m²/g, and 12 m²/g respectively. Generally speaking, smaller particles give rise to larger surface areas. However, in this study the particle sizes of all the catalysts were the about same, yet the catalysts synthetically prepared in pressurised $CO_2$ exhibited significantly smaller surface areas. Without wishing to be bound by theory, this may be due to the ZnGA crystals prepared under high pressure being more aggregated and highly compacted, resulting in relatively lower porosity, which appears to be confirmed by the SEM images.

Total pore volume and pore size distribution of the particles were analyzed using Barrett-Joyner-Halenda (BJH) model by using liquid nitrogen $N_2$ adsorption and desorption isotherm, to further understand the effect of solvent on the catalyst synthesis. ZnGA prepared in toluene (Cat. T) had a significantly higher $N_2$ uptake (volume adsorbed, cm$^3$/g), indicating the larger pore volume of this catalyst. Catalyst produced in toluene had more porosity compared to those prepared in accordance with the present invention, with pore diameters between 5 nm and 200 nm. The catalyst prepared in supercritical $CO_2$ demonstrated substantially lower $N_2$ uptake due to the relatively lower pore volume.

The activity of ZnGA catalysts can be improved by preparing the catalysts to have higher crystallinity and larger surface area. The catalyst prepared under high pressure $CO_2$ exhibits higher crystallinity than conventionally prepared catalysts, however, lower surface areas. However, the surface area may be increased by grinding the catalyst to lower particle sizes.

Copolymerization of $CO_2$ and Propylene Oxide

The activity of different catalysts was assessed for the synthesis of poly(propylene carbonate) from copolymerisation of $CO_2$ and propylene oxide. As shown in the following scheme, the copolymerisation of $CO_2$ and PO with ZnGA catalyst mainly results in the production of PPC accompanied with byproducts such as cyclic propylene carbonate and polyether. Both byproducts can be easily removed due to their high solubility in methanol and low solubility of PPC. Typically, methanol-soluble byproducts are less than 1%. ZnGA is also active for the homopolymerisation of propylene oxide to fabricate poly(propylene oxide) (PPO).

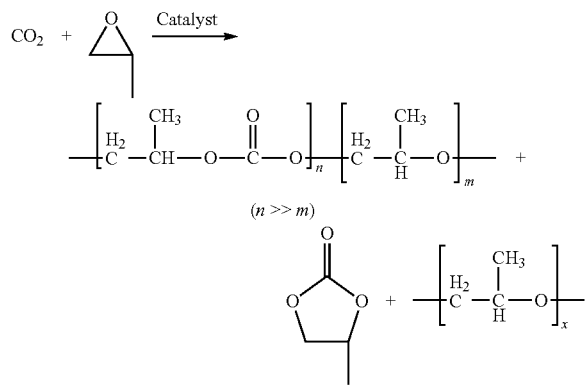

The optimum conditions reported for the copolymerization of PPC are using $CO_2$ at 50 bar and 60° C. for 40 hrs.

Figure 10:
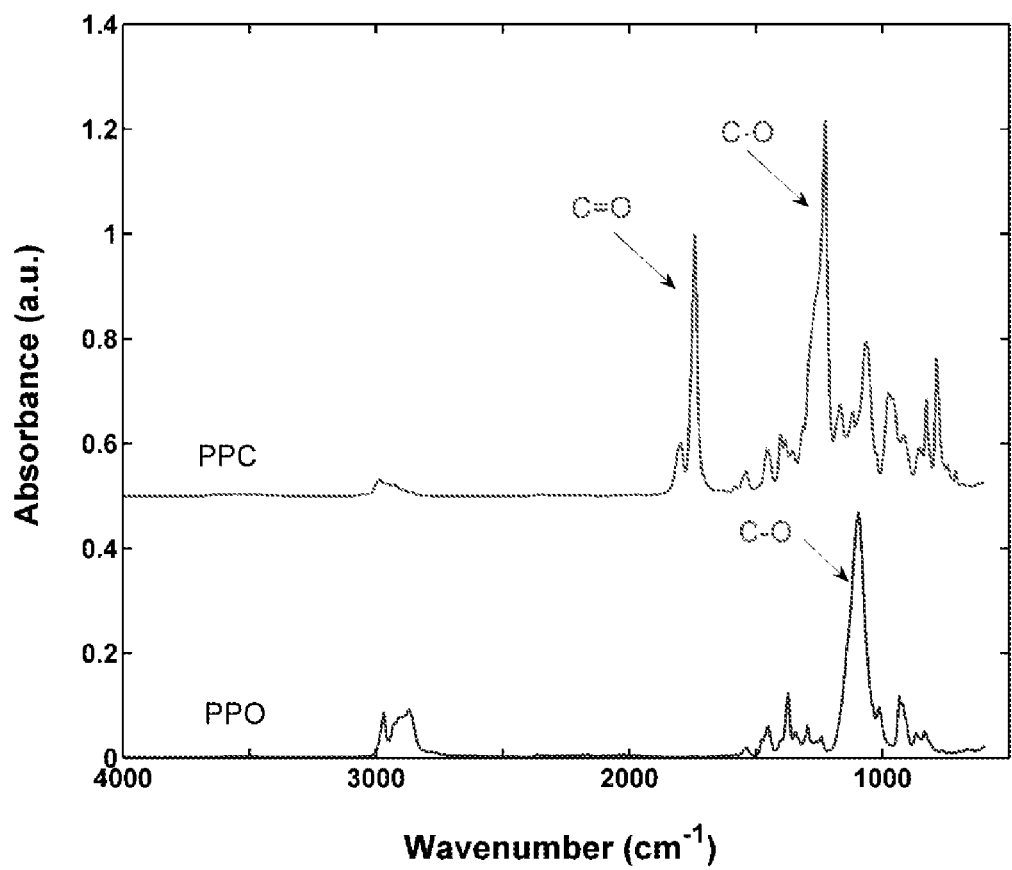
FIG. 10 shows FTIR spectra of PPC and PPO.

The FTIR spectra of PPC (the methanol insoluble polymer) and PPO is shown in FIG. 10. These results demonstrate that ZnGA catalyst synthetically prepared in pressurised $CO_2$ was effective for the synthesis of PPC. The peaks at wavenumber 1742 cm$^{-1}$ and 1227 cm$^{-1}$ indicate the presence of C=O group and the C—O group vibration absorbance in the chain of PPC respectively. The presence of peak 1096 cm$^{-1}$ and the absence of C=O bond absorbance suggests the formation PPO by using ZnGA catalyst.

Figure 11:
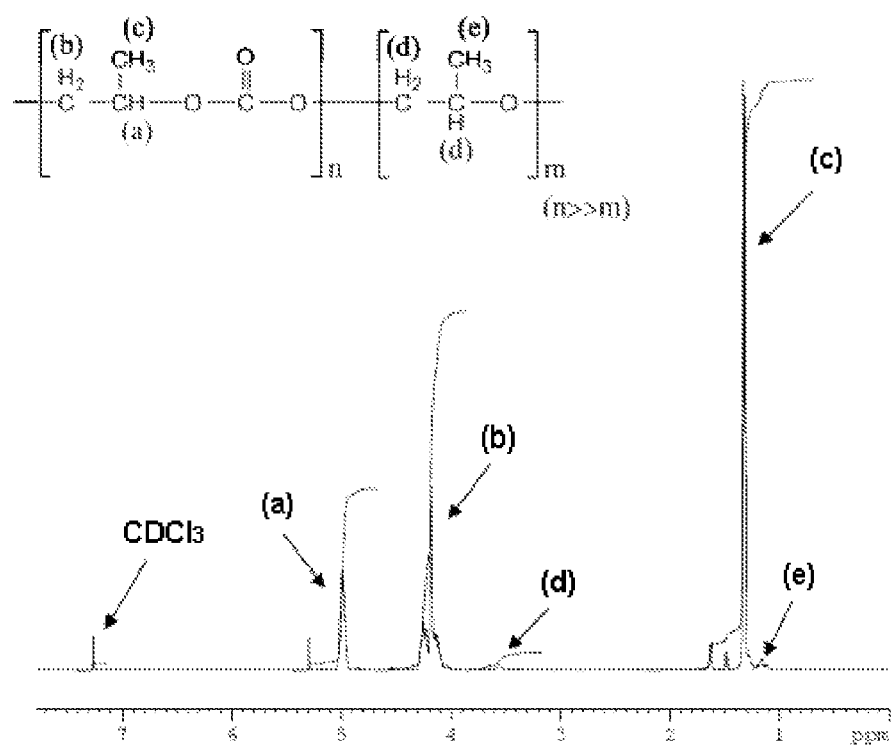
FIG. 11 shows $^1H$ and $^{13}C$ NMR spectra of PPC.
Figure 11:
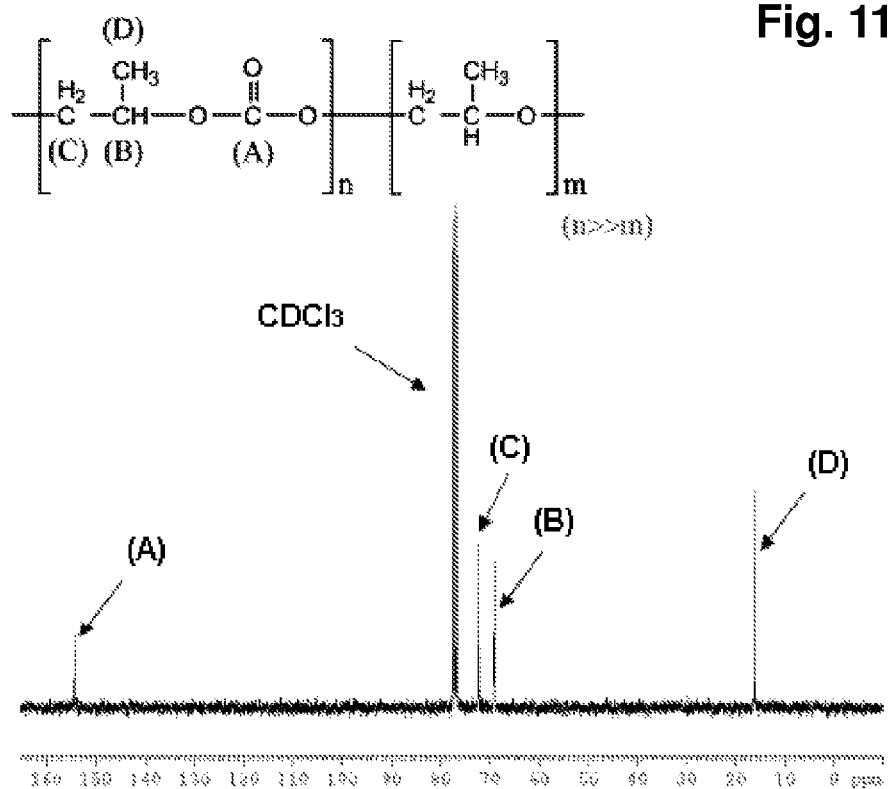
Figure 12:
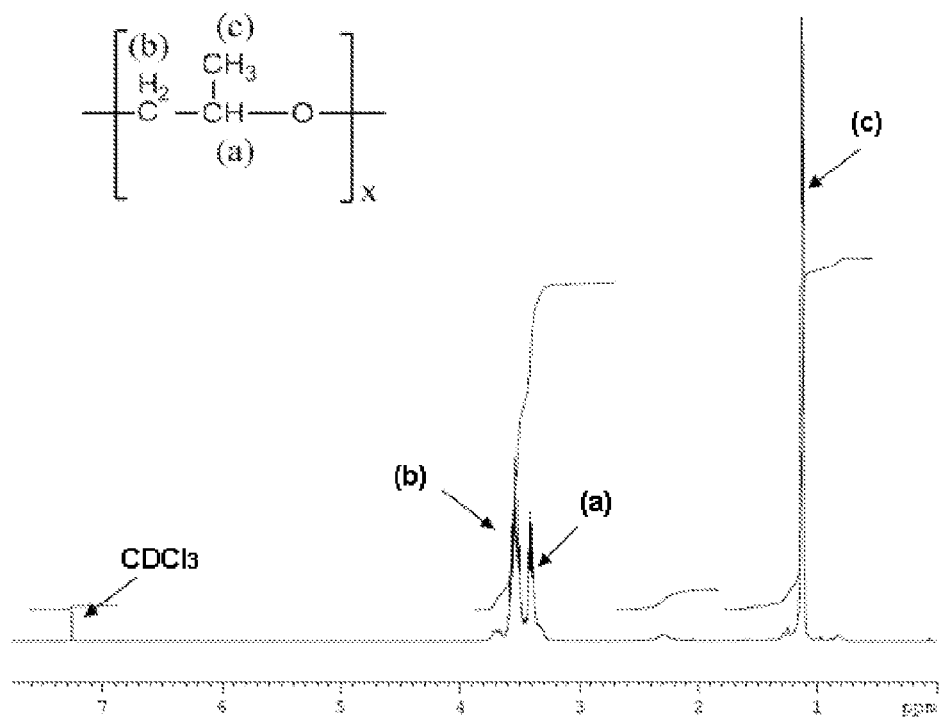
FIG. 12 shows $^1H$ and $^{13}C$ NMR spectra of PPO.
Figure 12:
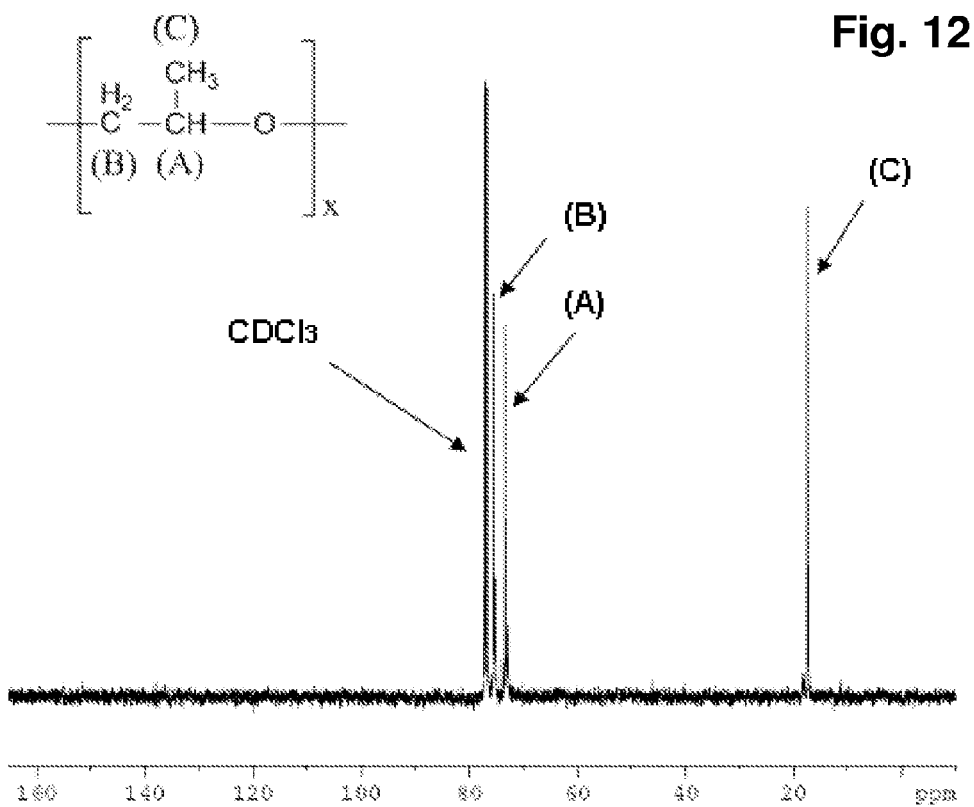

The polymers were further examined with NMR. Both $^1$H-NMR and $^{13}$C-NMR spectra for the methanol insoluble polymer products is shown in FIG. 11: $^1$H-NMR ($\delta$, CDCl$_3$), 1.31 (3H, CH$_3$), 4.18 (2H, CH$_2$CH), 4.98 (1H, CH$_2$CH); $^{13}$C-NMR ($\delta$, CDCl$_3$), 16.4 (CH$_3$), 69.0 (CH$_2$CH), 72.4 (CH$_2$CH), 154.3 (OCOO). The NMR spectra show that the polymer was PPC. The chemical shifts of 1.16 ppm (CH$_3$) and 3.40-3.80 ppm (1H, CH$_2$CH) observed in $^1$H-NMR spectrum correspond to the poly(propylene oxide) (PPO) unit, for PPO, $^1$H-NMR ($\delta$, CDCl$_3$), 1.14 (3H, CH$_3$), 3.56 (2H, CH$_2$CH), 3.40 (1H, CH$_2$CH); $^{13}$C-NMR ($\delta$, CDCl$_3$), 17.4 (CH$_3$), 73.3 (CH$_2$CH), 75.5 (CH$_2$CH) (FIG. 12).

TABLE 4

Results of copolymerization of $CO_2$ and PO

| Catalyst | Yield (g polymer/g ZnGA) | fc (mol %) |
| --- | --- | --- |
| Cat. T (toluene, 4 hrs) | 67.4 | 49.2 |
| Cat. 1 (50 bar, 4 hrs) | 66.2 | 49.4 |
| Cat. 2 (50 bar, 6 hrs) | 71.5 | 49.4 |
| Cat. 3 (100 bar, 4 hrs) | 74.2 | 49.5 |
| Cat. 4 (150 bar, 2 hrs) | 73.8 | 49.3 |

The activity of a heterogeneous catalyst is a function of its particle size, surface area and crystallinity. The yield of PPC copolymerisation was 67.4 g polymer/g catalyst when using ZnGA prepared in toluene. However, it was increased to 74 g polymer/g catalyst when using ZnGA prepared in $CO_2$ (see Table 4). The higher activity of catalyst prepared in $CO_2$ may result from its greater degree of crystallinity.

One-Pot Synthesis of the Catalyst and Polymer

In these experiments the catalyst produced under pressurised $CO_2$ was used for the synthesis of PPC. The results of NMR and FTIR analysis are shown in FIG. 10-12, which show that ZnGA catalyst was active for polymerisation, however the yield of the polymerisation reaction was slightly low (see Table 5). This is likely due to slight impurities. However, the one-pot process avoided using any toxic organic solvent and minimized the reaction steps, and therefore is cost effective compared to current methods, and has potential for large scale polymer production.

TABLE 5

Results of copolymerization of $CO_2$ and PO with one-pot process

| ZnGA | | | | |
| --- | --- | --- | --- | --- |
| Temp. (° C.) | Press. (bar) | Reaction time (hrs) | Copolymerisation | Yield (g polymer/g catalyst*) |
| 60 | 50 | 6 | 60° C., 50 bar, | 47.8 |
| 60 | 80 | 4 | 40 hrs, PO | 50.2 |
| 60 | 100 | 4 | 5 mL | 53.6 |
| 60 | 150 | 2 | | 52.3 |

*Catalyst is a mixture of ZnGA, unreacted GA and ZnO 0.5 mmol ZnO and 0.49 mmol GA were added in the start.

Synthesis of Other Catalysts Using High Pressure $CO_2$ Processes

The feasibility of using high pressure $CO_2$ for the synthesis of other catalysts was assessed. Several reactants were selected, namely adipic acid (AA) and 2-methylglutaric acid (2-MGA), which were reacted with zinc oxide to produce ZnAA and ZnMGA catalysts. The other catalyst investigated was the reaction between cobalt acetate and benzoic acid.

Figure 13:
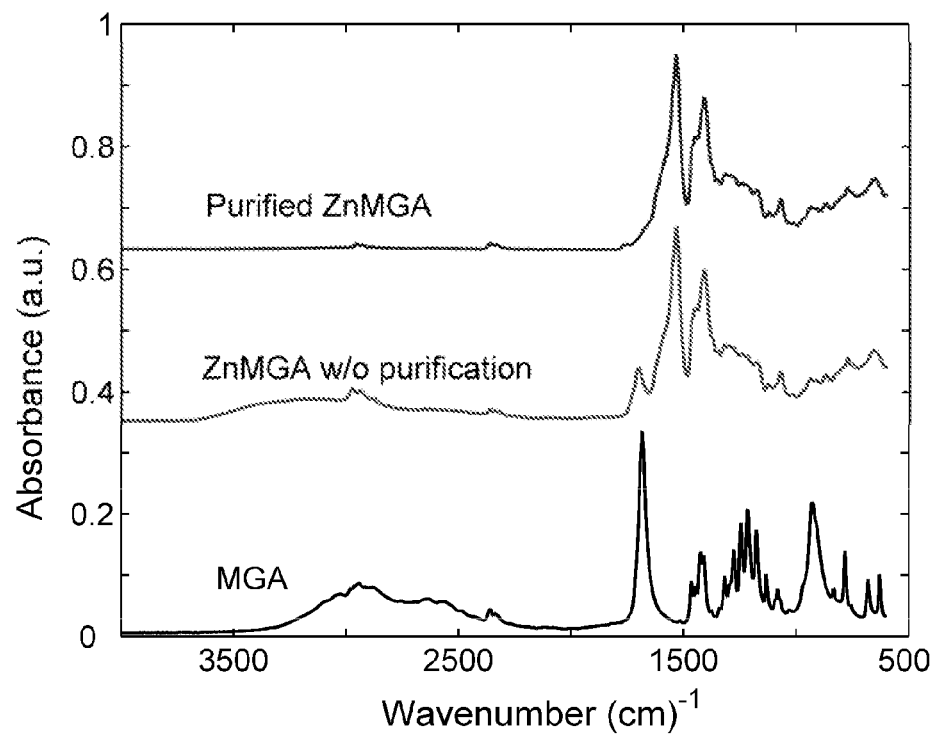
FIG. 13 shows FTIR spectra of MGA, ZnMGA without purification and the purified ZnMGA.
Figure 14:
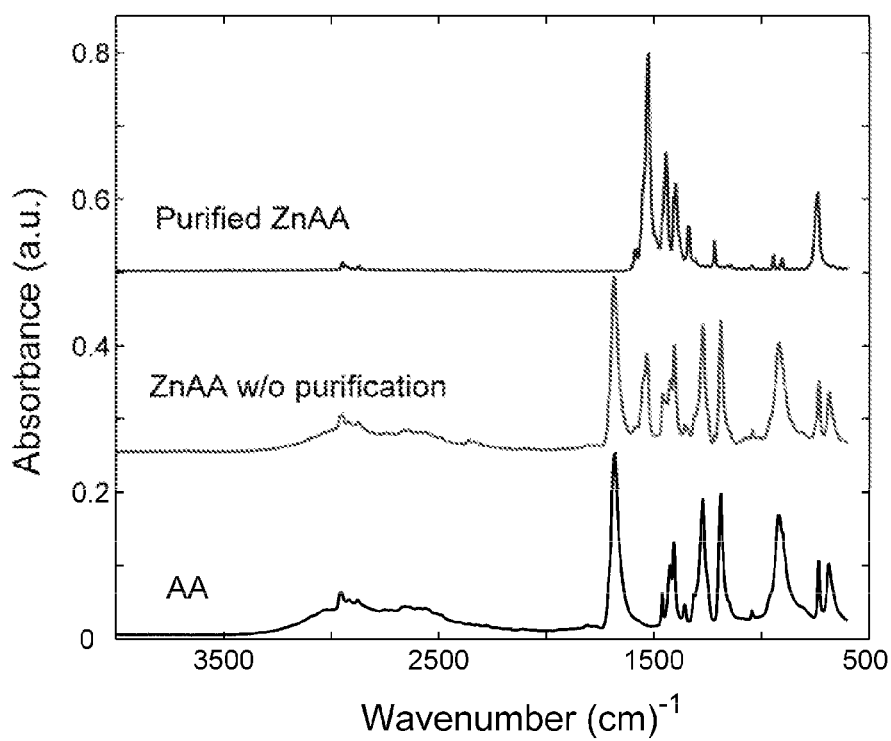
FIG. 14 shows FTIR spectra of AA, ZnAA without purification, and purified ZnAA.
Figure 15:
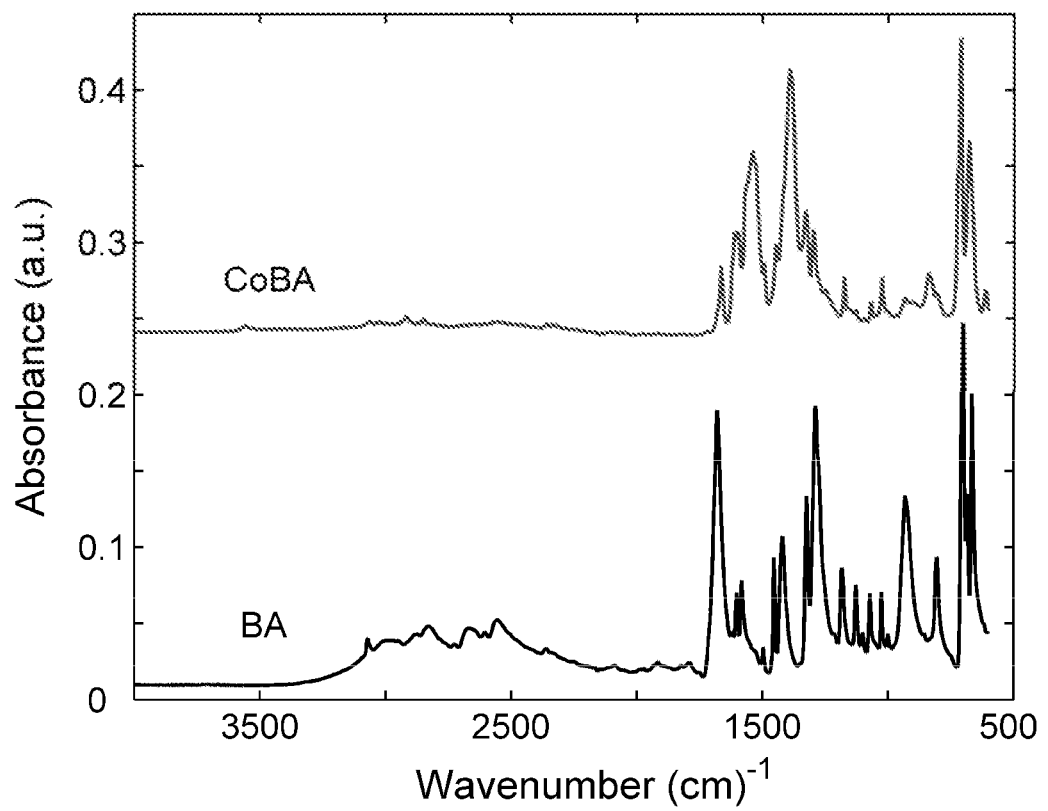
FIG. 15 shows FTIR spectra of BA, CoBA.

The reactions were carried out at 60° C. and 100 bar for a period of 6 hrs. The results of ATR-FTIR characterisation (see FIGS. 13-15) demonstrate that ZnAA, ZnMGA and CoBA were produced. The disappearance of peaks at 1,684 cm$^{-1}$ and presence of peak 1,585 cm$^{-1}$, 1,537 cm$^{-1}$ and 1,412 cm$^{-1}$ demonstrated the consumption of acid carbonyl (C=O) group and the formation of zinc-carboxylate bond (COO—) for both ZnMGA and ZnAA. In synthesis of CoBA the absence of peak at 1,679 cm$^{-1}$ and the presence of peak 1,541 cm$^{-1}$ demonstrated the consumption of acid carbonyl (C=O) group and the formation of cobalt-carboxylate bond (COO—).

As shown in Table 6, the yield of cobalt benzoate (CoBA) was higher than other catalysts, which can be attributed to the higher solubility of benzoic acid in $CO_2$ at the reaction conditions.

TABLE 6

Yield result of synthesis of catalyst ZnAA, ZnMGA, CoBA

| Reactants | Yield (%) |
|---|---|
| ZnO (4.5 mmol), 2-MGA (4.5 mmol) | 71.2 |
| ZnO (4.5 mmol), AA (4.5 mmol) | 77.5 |
| Co(OAc)$_2$ (mmol), BA (mmol) | 85.1 |

Although the invention has been described with reference to specific examples, it will be appreciated by those skilled in the art that the invention may be embodied in many other forms. In particular features of any one of the various described examples may be provided in any combination in any of the other described examples.

The claims defining the invention are as follows:

1. A method for producing an organometallic catalyst comprising:
   combining a polycarboxylic acid or anhydride and a metal-oxide, metal-hydroxide or metal-salt with a solvent at a temperature and pressure at which the solvent exists as a supercritical or near-critical fluid; and
   reacting said polycarboxylic acid or anhydride with said metal-oxide, metal-hydroxide or metal-salt for sufficient time and under sufficient temperature and pressure to produce said organometallic catalyst.

2. The method according to claim 1 wherein said polycarboxylic acid or anhydride is reacted with said metal-oxide, metal-hydroxide or metal-salt at temperatures of between about 40% to 150% of the critical temperature of said solvent, and pressures of between about 40% to 150% of the critical pressure of said solvent.

3. The method according to claim 2 wherein said solvent is in its supercritical state.

4. The method according to claim 2 wherein said solvent is in its near-critical state.

5. The method according to claim 1 wherein said solvent is selected from the group consisting of methane, ethane, ethylene, propylene, trifluorochloromethane, difluoromethane, isomers of tetrafluoroethane, pentafluoroethane, isomers of trifluoroethane, isomers of pentafluoropropane, difluorochloromethane, isomers of tetrafluorochloroethane, carbon dioxide, nitrogen, ammonia, nitrous oxide, water, refrigerants and mixtures of two or more thereof.

6. The method according to claim 1 wherein said solvent is free from toluene, benzene, xylene, acetone, methanol, chloroform, methylene chloride, dimethyl formamide, dimethyl sulfoxide, halogentated hydrocarbons, pyridine, ketones, aldehydes and alcohols.

7. The method according to claim 1 wherein the metal of the metal-oxide, metal-hydroxide or metal-salt is selected from the group consisting of zinc, cobalt, cadmium, chromium, nickel, magnesium, manganese, iron and aluminium.

8. The method according to claim 1 wherein the polycarboxylic acid or anhydride is selected from the group consisting of dicarboxylates, tricarboxylates tetracarboxylates and polymeric compounds with pendant carboxylate functions.

9. The method according to claim 8 wherein the polycarboxylic acid is selected from the group consisting of glutaric acid, 2,2-dimethylglutaric acid, 3,3-dimethylglutaric acid, 2-methylglutaric acid, 3-methylglutaric acid, 3-phenylglutaric acid, 2-ketoglutaric acid, 3-ketoglutaric acid, diglycolic acid, 3,3-tetramethyleneglutaric acid, adipic acid and monomethyl glutarate.

10. The method according to claim 8 wherein the polycarboxylic anhydride is selected from the group consisting of glutaric anhydride, 2,2-dimethylglutaric anhydride, 3,3-dimethylglutaric anhydride, 2-methylglutaric anhydride, 3-methylglutaric anhydride, 3-phenylglutaric anhydride, 2-ketoglutaric anhydride, adipic anhydride, 3-ketoglutaric anhydride, diglycolic acid, and 3,3-tetramethyleneglutaric anhydride.

11. The method according claim 1 wherein the reaction time is between about 0.5 to 40 hours.

12. The method according to claim 1 wherein the reaction temperature is between about 25 to 250° C.

13. The method according to claim 1 wherein the reaction pressure is between about 10 to 300 bar.

14. A formulation for producing an organometallic catalyst comprising:
   a solvent in its supercritical or near-critical state,
   a polycarboxylic acid or anhydride and
   a metal-oxide, metal-hydroxide or metal-salt.

15. A method for controlling one or more crystal characteristics of an organometallic material during synthesis of the organometallic material, wherein said characteristics are selected from the group consisting of crystallinity, particle size, shape, polymorphism and porosity,
   said method comprising:
   reacting a polycarboxylic acid or anhydride with a metal-oxide, metal-hydroxide or metal-salt in the presence of a solvent for sufficient time and under sufficient temperature and pressure to produce said organometallic material, wherein said solvent exists either as a supercritical or a near-critical fluid thereby controlling the crystal characteristics of the produced organometallic material.

* * * * *

UNITED STATES PATENT AND TRADEMARK OFFICE
CERTIFICATE OF CORRECTION

PATENT NO. : 8,507,708 B2  Page 1 of 1
APPLICATION NO. : 13/140695
DATED : August 13, 2013
INVENTOR(S) : Dehghani et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 234 days.

Signed and Sealed this

Fifteenth Day of September, 2015

Michelle K. Lee
*Director of the United States Patent and Trademark Office*